US012465726B2

(12) United States Patent
Antonucci et al.

(10) Patent No.: US 12,465,726 B2
(45) Date of Patent: Nov. 11, 2025

(54) SYSTEM AND METHOD FOR ASSEMBLY OF A LOW PROFILE PASSIVE PROTECTOR FOR AN I.V. CATHETER

(71) Applicant: Luther Needlesafe Products, LLC, Mission Viejo, CA (US)

(72) Inventors: Joseph G. Antonucci, Mission Viejo, CA (US); Joseph B. Antonucci, Mission Viejo, CA (US); Philip J. Antonucci, Mission Viejo, CA (US); John Muri, Mission Viejo, CA (US); Jeff Alan Burke, Murrieta, CA (US); Daniel Jason Velasco, Murrieta, CA (US); Joshua Alexander Sparks, Murrieta, CA (US); Kevin Martin Magrini, Murrieta, CA (US)

(73) Assignee: Luther Needlesafe Products, LLC, Mission Viejo, CA (US)

( * ) Notice: Subject to any disclaimer, the term of this patent is extended or adjusted under 35 U.S.C. 154(b) by 789 days.

(21) Appl. No.: 17/812,930

(22) Filed: Jul. 15, 2022

(65) Prior Publication Data

US 2023/0059216 A1 Feb. 23, 2023

Related U.S. Application Data

(60) Provisional application No. 63/235,055, filed on Aug. 19, 2021.

(51) Int. Cl.
*A61M 25/06* (2006.01)

(52) U.S. Cl.
CPC .... *A61M 25/0606* (2013.01); *A61M 25/0631* (2013.01); *A61M 25/0693* (2013.01); *A61M 2207/10* (2013.01)

(58) Field of Classification Search
CPC .......... A61M 25/0606; A61M 25/0631; A61M 25/0693; A61M 2207/10; A61M 25/0009; A61M 25/0034
See application file for complete search history.

(56) References Cited

U.S. PATENT DOCUMENTS 2,717,599 A 9/1955 Huber
3,448,740 A 6/1969 Frank
(Continued)

FOREIGN PATENT DOCUMENTS

CN 1146918 A 4/1997
CN 1046286 C 11/1999
(Continued)

OTHER PUBLICATIONS

Patent Cooperation Treaty, International Search Report and Written Opinion for International Application No. PCT/US22/40220, mailed Dec. 30, 2022, 6 pages.

*Primary Examiner* — JaMel M Nelson
*Assistant Examiner* — Erica Hartsell Funk
(74) *Attorney, Agent, or Firm* — Stetina Garred Brucker & Newboles

(57) ABSTRACT

A low-profile universal passive protector for an IV catheter includes a connector having a tubular body and a pair of arms pivotally connected thereto. The tubular body defines an end face and the connector includes a cavity extending from the end face. An elongate sheath is snap engageable to the tubular body. A spring is insertable within the connector cavity to extend between at least one of the pair of arms and the elongate sheath when received within the cavity. A slider is moveably coupled to the sheath. The slider includes a flashback chamber formed therein. A hypodermic needle is connected to the slider and is in fluid communication with the flashback chamber. The slider is moveable along the sheath between a first position and a second position, with
(Continued)

the hypodermic needle being drawn into the sheath as the slider moves from the first position toward the second position.

20 Claims, 25 Drawing Sheets

(56) References Cited

U.S. PATENT DOCUMENTS

| | | | | |
|---|---|---|---|---|
| 3,589,363 | A | | 6/1971 | Banko et al. |
| 3,612,050 | A | | 10/1971 | Sheridan |
| 3,645,268 | A | | 2/1972 | Capote |
| 3,780,733 | A | | 12/1973 | Martinez |
| 4,343,305 | A | | 8/1982 | Bron |
| 4,547,194 | A | * | 10/1985 | Moorehead ....... A61M 25/0014 604/905 |
| 4,549,879 | A | | 10/1985 | Groshong et al. |
| 4,565,545 | A | | 1/1986 | Suzuki |
| 4,626,240 | A | | 12/1986 | Edelman et al. |
| 4,702,260 | A | | 10/1987 | Wang |
| 4,747,831 | A | | 5/1988 | Kulli |
| 4,762,516 | A | | 8/1988 | Luther et al. |
| 4,763,667 | A | | 8/1988 | Manzo |
| 4,767,407 | A | | 8/1988 | Foran |
| 4,781,691 | A | | 11/1988 | Gross |
| 4,790,828 | A | | 12/1988 | Dombrowski et al. |
| 4,795,446 | A | | 1/1989 | Fecht |
| 4,808,156 | A | | 2/1989 | Dean |
| 4,841,007 | A | | 6/1989 | Zdrahala et al. |
| 4,869,717 | A | | 9/1989 | Adair |
| 4,935,480 | A | | 6/1990 | Zdrahala et al. |
| 4,936,826 | A | | 6/1990 | Amarasinghe |
| 4,944,728 | A | | 7/1990 | Carrell et al. |
| 4,950,252 | A | | 8/1990 | Luther et al. |
| 4,964,854 | A | | 10/1990 | Luther |
| 4,978,344 | A | | 12/1990 | Dombrowski et al. |
| 4,994,041 | A | | 2/1991 | Dombrowski et al. |
| 5,106,376 | A | | 4/1992 | Mononen et al. |
| 5,135,502 | A | | 8/1992 | Koenig, Jr. et al. |
| 5,137,515 | A | | 8/1992 | Hogan |
| 5,215,525 | A | | 6/1993 | Sturman |
| 5,226,883 | A | | 7/1993 | Katsaros et al. |
| RE34,416 | E | | 10/1993 | Lemieux |
| 5,295,974 | A | | 3/1994 | O'Laughlin |
| 5,295,980 | A | | 3/1994 | Ersek |
| 5,300,045 | A | | 4/1994 | Plassche, Jr. |
| 5,312,345 | A | | 5/1994 | Cole |
| 5,312,371 | A | | 5/1994 | Dombrowski et al. |
| 5,330,434 | A | | 7/1994 | Mcfarlane |
| 5,334,185 | A | | 8/1994 | Giesy et al. |
| 5,403,283 | A | | 4/1995 | Luther |
| 5,419,766 | A | | 5/1995 | Chang et al. |
| 5,531,701 | A | | 7/1996 | Luther |
| 5,533,988 | A | | 7/1996 | Dickerson et al. |
| 5,558,651 | A | | 9/1996 | Crawford et al. |
| 5,569,202 | A | | 10/1996 | Kovalic et al. |
| 5,569,217 | A | | 10/1996 | Luther |
| 5,575,777 | A | | 11/1996 | Cover et al. |
| 5,599,310 | A | | 2/1997 | Bogert |
| 5,611,781 | A | | 3/1997 | Sircom et al. |
| 5,634,913 | A | | 6/1997 | Stinger |
| 5,662,610 | A | | 9/1997 | Sircom |
| 5,683,370 | A | | 11/1997 | Luther et al. |
| 5,685,855 | A | | 11/1997 | Erskine |
| 5,688,249 | A | | 11/1997 | Chang et al. |
| 5,718,688 | A | | 2/1998 | Wozencroft |
| 5,830,190 | A | | 11/1998 | Howell |
| 5,865,806 | A | | 2/1999 | Howell |
| 5,891,098 | A | | 4/1999 | Huang |
| 5,913,848 | A | | 6/1999 | Luther et al. |
| 5,916,208 | A | | 6/1999 | Luther et al. |
| 5,935,108 | A | | 8/1999 | Katoh et al. |
| 5,957,893 | A | | 9/1999 | Luther et al. |
| 5,989,220 | A | | 11/1999 | Shaw et al. |
| 6,004,294 | A | | 12/1999 | Brimhall et al. |
| 6,056,718 | A | | 5/2000 | Funderburk et al. |
| 6,090,078 | A | | 7/2000 | Erskine |
| 6,203,533 | B1 | | 3/2001 | Ouchi |
| 6,213,978 | B1 | | 4/2001 | Voyten |
| 6,217,527 | B1 | | 4/2001 | Selmon et al. |
| 6,379,333 | B1 | | 4/2002 | Brimhall et al. |
| 6,520,938 | B1 | | 2/2003 | Funderburk et al. |
| 6,595,954 | B1 | | 7/2003 | Luther et al. |
| 6,981,965 | B2 | | 1/2006 | Luther et al. |
| 7,753,887 | B2 | | 7/2010 | Botich et al. |
| 8,057,439 | B2 | | 11/2011 | Di Fiore |
| 2003/0083620 | A1 | | 5/2003 | Luther et al. |
| 2004/0167474 | A1 | | 8/2004 | Meng et al. |
| 2007/0088279 | A1 | | 4/2007 | Shue et al. |
| 2007/0161940 | A1 | | 7/2007 | Blanchard et al. |
| 2007/0191776 | A1 | | 8/2007 | Bialecki et al. |
| 2008/0287876 | A1 | | 11/2008 | Shue et al. |
| 2010/0056862 | A1 | | 3/2010 | Bakos |
| 2010/0081986 | A1 | | 4/2010 | Matson et al. |
| 2011/0001557 | A1 | | 1/2011 | Huang et al. |
| 2011/0015573 | A1 | | 1/2011 | Maan et al. |
| 2011/0168171 | A1 | | 7/2011 | Tsuboko et al. |
| 2012/0245562 | A1 | | 9/2012 | Bihlmaier |
| 2013/0053826 | A1 | | 2/2013 | Shevgoor |
| 2013/0060137 | A1 | | 3/2013 | Uber, III et al. |
| 2018/0339131 | A1 | | 11/2018 | Muse et al. |
| 2019/0184141 | A1 | | 6/2019 | Antonucci |

FOREIGN PATENT DOCUMENTS

| | | | | | |
|---|---|---|---|---|---|
| CN | 1173376 | C | | 10/2004 | |
| CN | 201101798 | Y | | 8/2008 | |
| CN | 111840748 | A | | 10/2020 | |
| EP | 343803 | A2 | | 11/1989 | |
| EP | 475375 | B1 | | 12/1994 | |
| EP | 645159 | A1 | | 3/1995 | |
| EP | 747083 | A2 | | 12/1996 | |
| EP | 791370 | A1 | | 8/1997 | |
| EP | 734739 | A3 | | 7/1998 | |
| EP | 830872 | B1 | | 5/2003 | |
| EP | 1110576 | B1 | | 5/2004 | |
| JP | 08257129 | A | | 10/1996 | |
| JP | 09099069 | A | | 4/1997 | |
| JP | 2962268 | B2 | | 10/1999 | |
| WO | 9533509 | A1 | | 12/1995 | |
| WO | 9908742 | A1 | | 2/1999 | |
| WO | 0006226 | A1 | | 2/2000 | |
| WO | 0013728 | A1 | | 3/2000 | |
| WO | 2004045701 | A1 | | 6/2004 | |
| WO | 2007098355 | A1 | | 8/2007 | |
| WO | WO-2019201859 | A1 | * | 10/2019 | ........ A61M 25/0012 |

* cited by examiner

SYSTEM AND METHOD FOR ASSEMBLY OF A LOW PROFILE PASSIVE PROTECTOR FOR AN I.V. CATHETER

CROSS-REFERENCE TO RELATED APPLICATIONS

This application claims the benefit of U.S. Provisional Application No. 63/235,055, filed Aug. 19, 2021, the contents of which are expressly incorporated herein by reference.

STATEMENT RE: FEDERALLY SPONSORED RESEARCH/DEVELOPMENT

Not Applicable

BACKGROUND

1. Technical Field

The present disclosure relates generally to a system and method of manufacturing a passive protector for an intravenous (I.V.) catheter.

2. Related Art

It is well known in the medical profession that various medical treatments and procedures oftentimes require the insertion or withdrawal of fluid from a patient. Intravenous needles are commonly employed to achieve such insertion or withdrawal of fluid. However, in some instances, the needle may be required to remain in the patient for an extended period of time, such as when introducing or withdrawing large amounts of fluid. Under these circumstances, metal needles are typically unfavorable due to their rigid structure and sharp distal tip which can cause trauma to the patient's vein. In view of the disadvantages associated with metal needles, medical professionals commonly use a catheter for such applications.

A conventional catheter typically includes a generally flexible tube having a hard/rigid distal tip. The catheter is typically inserted into a patient's vein using a catheter introduction device. Various catheter introduction devices have been developed and include through-the-needle catheters, as well as over-the-needle catheters. A through-the-needle catheter is inserted into an anatomical passage of the patient through the use of a cannula, which typically includes an elongate, metal needle which punctures the skin, tissue and vein wall to provide a path for placement of the catheter in the vein. When the needle pierces the vein, blood will "flashback" through the needle and into a flashback chamber typically located at the proximal end of the needle. Thus, the "flashback" is an indication to the medical technician that the needle has been properly inserted into the vein. At this point, the catheter is maintained stationary within the vein and the needle is withdrawn and removed from the catheter. The needle may have score lines formed therein to allow a medical technician to tear or pull the needle apart to remove the needle from the catheter once the catheter is removed from the patient.

Over-the-needle catheters are also commonly used by medical technicians, and typically include a thin catheter having a hub attached to its proximal end. The catheter is advanced over a rigid cannula, such as a needle, with the cannula and catheter being simultaneously advanced into a desired anatomical passage of a patient. Once the catheter has been inserted into the anatomical passage of the patient, the cannula is typically removed from the catheter by retracting the cannula through the catheter. The action of retracting the cannula can undesirably expose the medical technician as well as the patient to accidental contact with the cannula, particularly the piercing tip of the needle. Such accidental needle sticks are a serious concern in view of such diseases as Acquired Immune Deficiency Syndrome ("AIDS"), which can be transmitted through the exchange of bodily fluids with an infected person. In particular, a needle that has been used to place a catheter in the vein of an AIDS infected person may be a vehicle for transmission of the disease to the medical technician.

A number of protective devices have been developed recently to help reduce the incidence of disease and transmission through needle sticks. Many of the protective devices employ a protective, elongate sheath into which the needle is retracted as the needle is withdrawn from the patient. Along these lines, when the needle is withdrawn, its sharp distal tip is safely enclosed within the sheath, which is typically formed from a rigid material.

Operation of the protective devices generally includes an actuation mechanism connected to the needle, which is operated by the fingers of the medical technician. The technician uses various structures on the protective device to push against or pull on for retracting the needle within the sheath. However, in many protective devices, the flashback chamber is positioned in a manner which makes it difficult for the medical technician to easily grasp and manipulate the protective device in its intended manner. Such difficulty may lead to improper operation of the protective device, which may lengthen the process of inserting the catheter, or compromise the protective nature of the device.

Another deficiency associated with conventional protective devices pertains to the manufacture and assembly thereof. Conventional protective devices may include several components that require tedious and time-consuming assembly. As such, the cost and time associated with assembling conventional protective devices may be significant.

In view of such deficiencies, a passive protector for an intravenous catheter has been developed by Luther Needlesafe Products, LLC, and which is the subject of U.S. patent application Ser. No. 17/187,103, the contents of which are expressly incorporated herein by reference. The present disclosure relates to various systems and methods for quickly and easily assembling the passive protector for the intravenous catheter, as will be discussed in more detail below.

BRIEF SUMMARY

According to an aspect of the disclosure, there is provided a system and method of forming a shaped, hardened end portion of an over the needle catheter. An unfinished catheter includes a hard catheter body inserted in the end of a soft catheter body. An opposite end of the soft catheter body is placed on a mandrel having an elongate narrow portion, which is received in the soft catheter body. The mandrel is urged toward a forming body, which forms the hard catheter body and the adjacent portion of the soft catheter body into a desired profile.

Another aspect of the disclosure relates to a system and method of connecting a ferrule to the soft catheter. A mandrel is used including a core pin, a base, and a magnet. A ferrule is placed on the core pin, and the soft catheter is then loaded on the core pin, such that the ferrule is captured between a wide portion of the core pin and the soft catheter.

The mandrel is loaded on a pressing machine, which when actuated, causes a pair of gripping arms to apply opposing gripping forces on the soft catheter while a pressing assembly moves toward the gripping arms to urge a portion of the ferrule into the soft catheter.

Another aspect of the disclosure relates to a system and method of connecting a hub to the soft catheter. A mandrel is used including a core pin, a base, and a magnet. A hub is placed on the core pin, and the soft catheter, having already been connected to a ferrule, is then loaded on the core pin, such that the ferrule is captured between a wide portion of the core pin and the hub. The mandrel is loaded on a pressing machine, which when actuated, causes a pressing assembly moves toward a fork to urge the hub into engagement with the ferrule.

Another aspect of the disclosure relates to a system and method of inserting a vent plug in a vent opening in a slider and wiping a hypodermic needle, connected to the slider, with a lubricant. A device includes a plug feed wheel having openings formed therein, each being sized to receive a respective vent plug. A push rod is sized and position to push a vent plug from the plug feed wheel into a vent opening, when the push rod, vent plug and vent plug opening are axially aligned with each other. The device additionally includes a pair of wipers that may concurrently wipe lubricant on the need from opposed sides of the need. The wiping operation may occur subsequent to insertion of the vent plug into the vent plug opening.

A further aspect of the disclosure relates to a system and method of completing a final assembly of the passive protector. A sheath holder may engage with a sheath, and a slider holder may hold the slider in axial alignment with the sheath. The sheath holder may move toward an intermediate carriage, which may be driven by the sheath holder and may facilitate press-fit engagement between the slider and the sheath. The intermediate carriage may urge the needle, connected to the slider, through a spring, a connector, the hub and catheter, which may be positioned in alignment on the device. A manual slider may be pivoted from a first pivot position toward a second pivot position, and then slid from a first slide position to a second slid position to drive the assembled passive protector into a cover.

According to one embodiment, a method of assembling a low-profile passive protector includes forming a hard tubular portion and a soft tubular portion to form an integral catheter having a prescribed contour. A ferrule is pressed into the catheter and a hub is attached to the catheter such that the ferrule facilitates attachment of the hub to the catheter. A vent plug is inserted into a slider and the slider is connected to the catheter.

The forming step may include placing the hardened tubular portion inside the soft tubular portion. The method may additionally include inserting a mandrel through the hard tubular portion and the soft tubular portion. The mandrel may be moved toward a forming body to facilitate contact between the forming body and the hard tubular portion. The forming body may be heated to facilitate melting of at least a portion of the hard tubular portion when the hard tubular portion is in contact with the mandrel.

The pressing step may include placing the ferrule on a mandrel having a pin insertable through the ferrule and the catheter.

The ferrule used in the pressing step may include a wide portion and a narrow portion, with the narrow portion being pressable into the soft tubular portion of the catheter. The method may additionally include moving the mandrel toward a gripping element configured to press a segment of the soft tubular portion over the narrow portion of the ferrule in response to such movement of the mandrel relative to the gripping element. The method may additionally include aligning the mandrel with the gripping element using magnetic attraction between the mandrel and a lower press plate associated with the gripping element. The method may also comprise raising the lower press plate toward the gripping element.

The hub used in the attaching step may include a proximal end face, a distal end face, an internal opening extending between the proximal end face and the distal end face and extending around a central axis, and an internal rib extending into the opening from an inner surface thereof. The attaching step may include loading the ferrule and catheter onto a core pin and placing the hub over the core pin and catheter such that a majority of the core pin and the catheter protrude from the hub, and the ferrule is located in the internal opening of the hub. The attaching step may further include pressing the ferrule beyond the internal rib.

The inserting step may include aligning the vent plug with a push rod. The alignment of the vent plug with the push rod may include rotating a plug feed wheel configured to carry the vent plug, until the vent plug is aligned with the push rod, the push rod being configured to be moveable relative to the plug feed wheel, the vent plug, and the slider. The method may also include actuating the push rod to push the vent plug into the vent plug opening.

The slider may include a hypodermic needle attached thereto, and the method further comprising the step of wiping the hypodermic needle with a lubricant.

The method may also include placing the slider in a slider holder, placing a sheath in a sheath holder, and causing the sheath holder to move toward to the slider holder to facilitate engagement between the sheath and the slider.

The method may further comprise placing a connector having a pair of arms in a connector holder, placing the slider in a slider holder aligned with a carriage moveable relative to the connector holder, and causing the carriage to move to carry the slider into engagement with the connector.

The method may additionally include forming a sub-assembly including the slider, a sheath, and a connector, with the slider being disposed between the sheath and the connector. A cover may be connected to the sub-assembly using a manually actuated slide-press configured to slide the sub-assembly into the cover.

The presently contemplated embodiments will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of the presently preferred embodiments of the disclosure, and is not intended to represent the only form in which the present devices may be developed or utilized. It is to be understood, however, that the same or equivalent functions may be accomplished by different embodiments that are also intended to be encompassed within the spirit and scope of the disclosure. It is further understood that the use of relational terms such as first, second, and the like are used solely to distinguish one from another entity without necessarily requiring or implying any actual such relationship or order between such entities.

Figure 1:
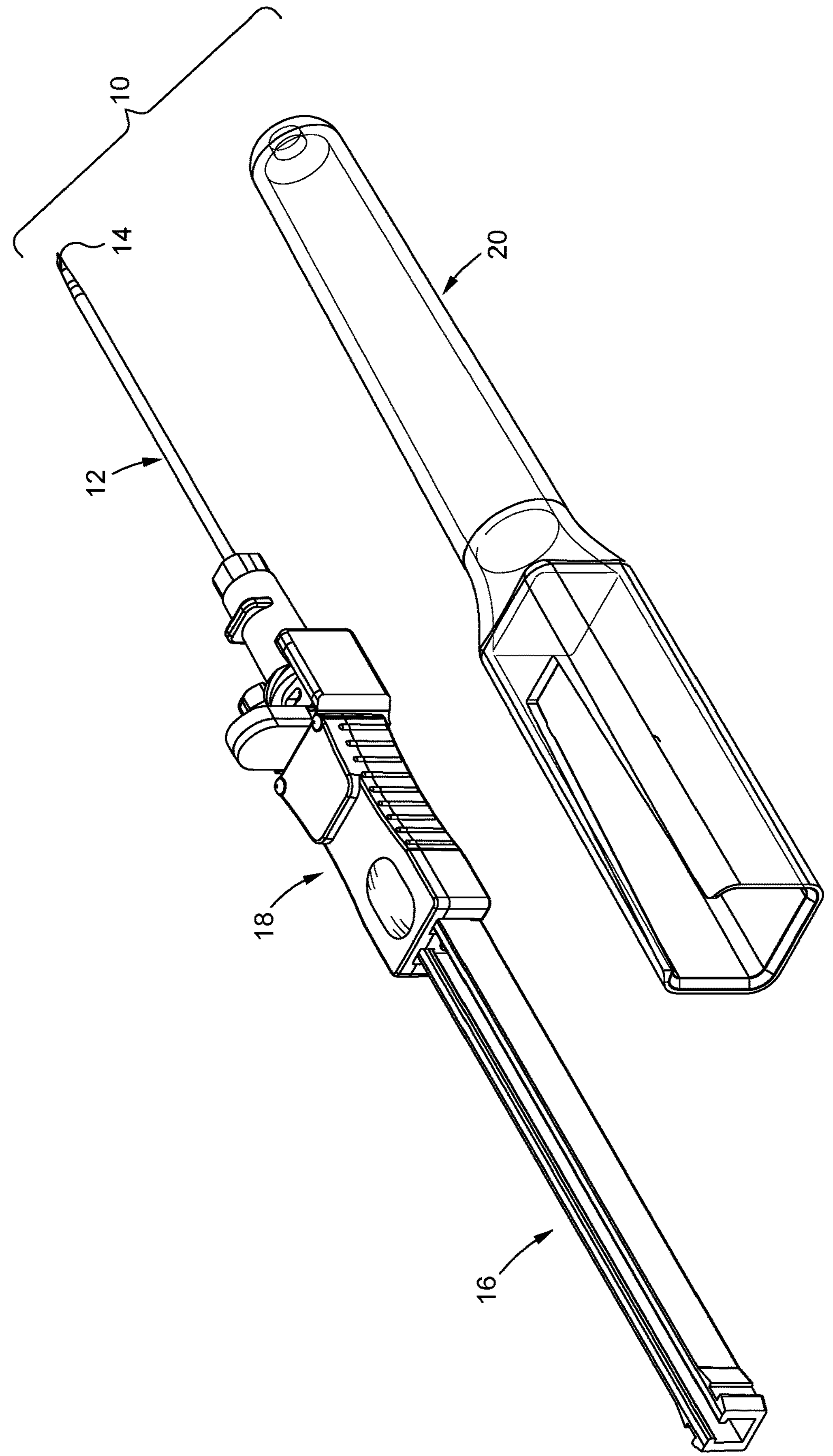
FIG. 1 is an upper perspective view of a universal passive protector with a cover removed to expose a hypodermic needle and an over-the-needle catheter.
Figure 2:
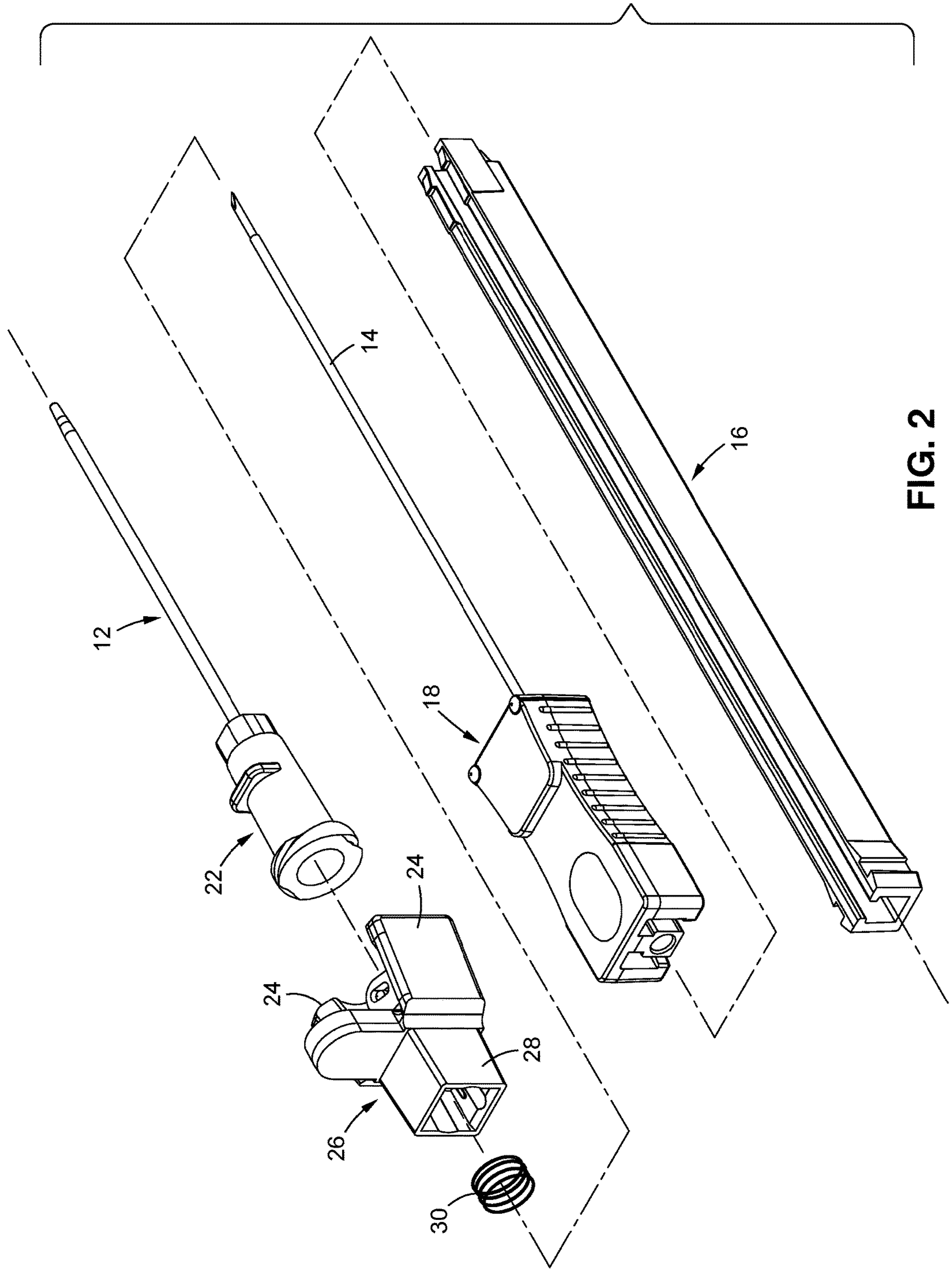
FIG. 2 is a rear, exploded, upper perspective view of the universal passive protector.

Referring now to FIG. 1, there is shown a low-profile universal passive protector 10 for use in inserting an over-the-needle catheter 12 into a patient. The universal passive protector 10 generally includes a hypodermic needle 14 that is configured to be withdrawn into a sheath 16 in response to movement of a slider 18 along the sheath 16 from a deployed position to a retracted position. The universal passive protector 10 may include a detachable cover 20 that may be placed over the needle 14 and catheter 12 before using the protector 10 to protect a medical professional from an inadvertent needle stick. FIG. 1 shows the cover 20 extending over the needle 14 and catheter 12. FIG. 2 is an exploded view showing the passive protector 10, without the cover 20. As can be seen, the catheter 12 is connected to a hub 22, which is releasably connected to a pair of arms 24 that are part of a connector 26. Opposite the arms 24, on the connector 26, is a quadrangularly shaped, tubular body 28 that receives a spring 30. The sheath 16 is connected to the tubular body 28, and the slider 18 is slidably connected to the sheath 16. As the slider 18 is moved from a deployed position toward a retracted position, the needle 14 is drawn into the sheath 16, and the arms 24 are pivoted from a closed position to an open position to release the hub 22.

Additional information regarding use of the catheter 12 is described in U.S. Pat. No. 8,956,328, entitled Low Profile Passive Protector For An I.V. Catheter, the content of which is expressly incorporated herein by reference.

Various aspects of the present disclosure relate to several systems and methods for assembling the universal passive protector 10. Referring first to FIGS. 3-7, there is depicted a catheter forming system 40 for forming a hardened tip at the end of the catheter 12. The system 40 may include a mandrel 42, a drive mechanism 44, and a forming mechanism 46, which collectively form the catheter 12 into the desired shape.

Figure 3:
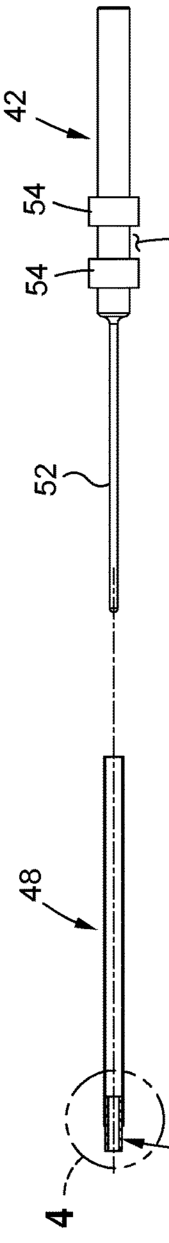
FIG. 3 is an exploded view of an unfinished catheter segment and a mandrel used to shape the catheter segment.
Figure 4:
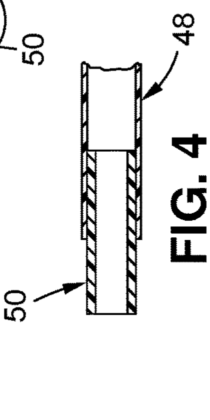
FIG. 4 is an enlarged, cross sectional view of a distal end portion of the unfinished catheter segment.
Figure 5:
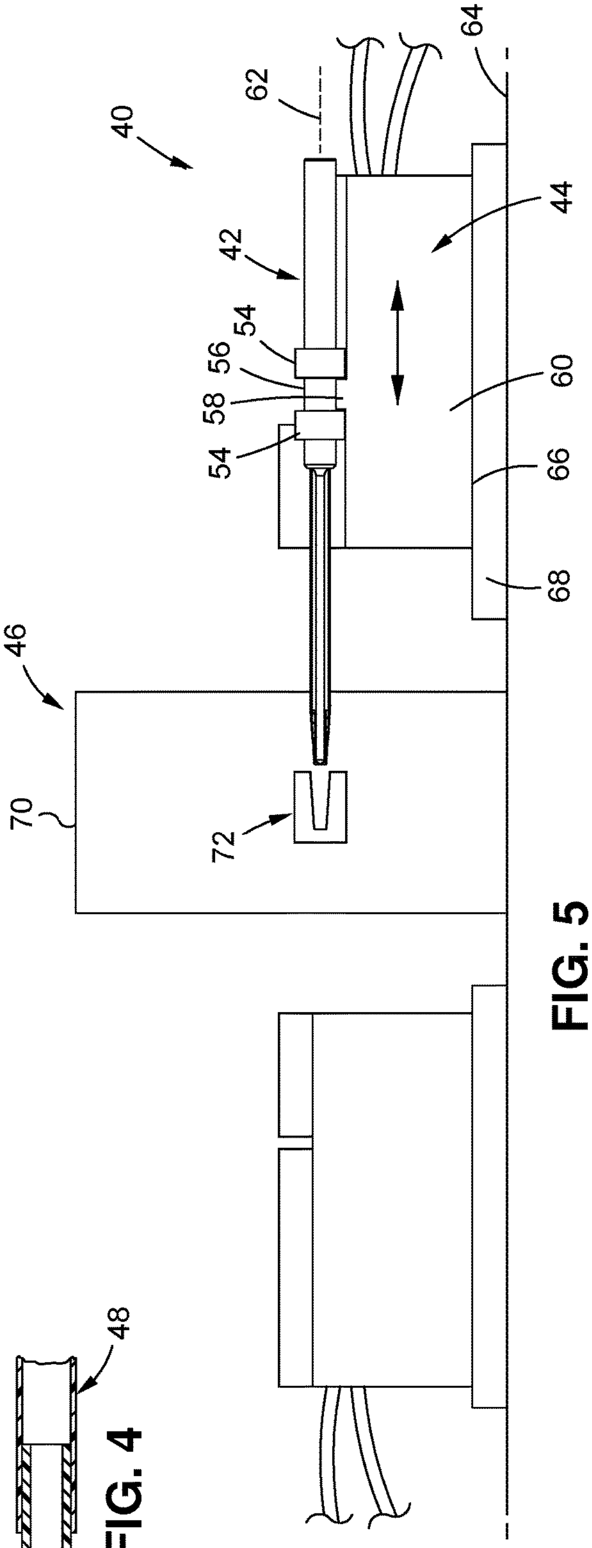
FIG. 5 is a side view of a catheter on the mandrel aligned with a forming mechanism for forming the distal end portion of the catheter.

The catheter 12 is formed from a soft portion of tubular material (e.g., a soft tubular portion) and a hard portion of tubular material (e.g., a hard tubular portion). FIG. 3 shows a soft tubular portion 48 and a hard tubular portion 50 inserted within the soft tubular portion 48 adjacent a distal end of the soft tubular portion 48. In this regard, the inner diameter of the soft tubular portion 48 may be slightly larger than the outer diameter of the hard tubular portion 50 to accommodate the hard tubular portion 50. The soft tubular portion 48 may be of sufficient resiliency to expand around the hard tubular portion 50 to accommodate receipt of the hard tubular portion 50 within the soft tubular portion 48. When the hard tubular portion 50 is received within the soft tubular portion 48, approximately half of the hard tubular portion 50 will reside within the soft tubular portion 48, while the remaining half of the hard tubular portion 50 will protrude tout of the soft tubular portion 48.

The soft tubular portion 48 may include an open end, opposite hard tubular portion 50, which may be aligned with the mandrel 42, which receives the soft tubular portion 48. The mandrel 42 may include an elongate shaft 52 sized and configured to be received within the soft tubular portion 48 and the hard tubular portion 50. In this regard, the elongate shaft 42 may be of sufficient length to extend through the soft tubular portion 48, and through at least some, if not all, of the hard tubular portion 50. The elongate shaft 52 may be rigid, and capable of providing an internal support structure upon which the soft tubular portion 48 and hard tubular portion 50 may be worked to achieve a desired configuration and contour, as will be explained in more detail below.

After the mandrel 42 has been inserted into the soft and hard tubular portions 48, 50, the mandrel 42 may be placed on the drive mechanism 44. To facilitate engagement between the mandrel 42 and the drive mechanism 44, the mandrel 42 may include a pair of ribs 54, spaced from each other, as well as being spaced from the elongate shaft 52, with the pair of ribs 54 defining a circumferential groove 56 or cavity. The circumferential groove 56 may be sized to engage with a protrusion 58 or other complementary structure formed on the drive mechanism 44. In the exemplary embodiment, the drive mechanism 44 includes a protrusion 58 having a width that corresponds to the space between the pair of ribs 54 on the mandrel 42, and a height that corresponds to the depth of the circumferential groove 56.

The protrusion 58 on the drive mechanism 44 may be formed on a main body 60 that is moveable along a drive axis 62 that is generally parallel to a support surface 64, such as a workbench or table. In this regard, the drive mechanism 44 may include a lower surface 66 that may be placed adjacent the support surface 64, with the drive axis 62 being generally parallel to the lower surface 66. In one embodiment, the lower surface 66 is translatable over a base body 68 that rests on the support surface 64. The base body 68 may include one or more grooves which may receive a rib or protrusion (not shown) formed on the main body 60 to guide the main body 60 between a first, retracted position, and a second, driven position.

The forming mechanism 46 is spaced from the drive mechanism 44 and includes a housing 70 and forming body 72 located within the housing 70. The forming body 72 includes a contoured surface that mimics the desired outer contour of the hardened tip of the catheter 12.

During use of the catheter forming system 40, elongate shaft 52 of the mandrel 42 is inserted into the open end of the soft tubular portion 48 and advanced along the length of the soft tubular portion 48 and into the hard tubular portion 50. In other words, the two assembled catheter tubes (e.g., the hard tubular portion 50 inside the soft tubular portion 48) may be loaded (slid) onto the elongate shaft 52, which may conform to the inner profile of the assembled catheter tubes (such as the inner profile of the soft tubular portion 48 and hard tubular portion 50 depicted in FIG. 4).

Figure 7:
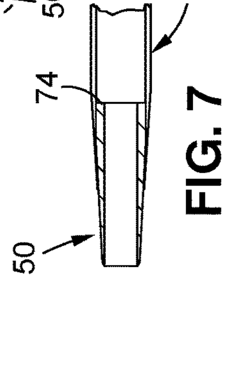
FIG. 7 is an enlarged, cross sectional view of the distal end portion of the shaped catheter segment.

The mandrel 42 is then placed on the drive mechanism/cradle 44, with the protrusion 58 on the drive mechanism 44 being received between the ribs on the mandrel. When the mandrel 42 is placed on the drive mechanism 44, the main body 60 of the drive mechanism 44 is in the retracted position. The cradle 44 positions the assembled catheter tubes 48, 50 on the mandrel 42 at the front of the forming mechanism 46 at the face of the mold cavity/die/forming body 72. The interior of the mold cavity/die 72 may be machined or otherwise configured to have the profile/shape of the finished catheter tip, as shown in FIG. 7.

The main body 60 is then actuated to transition from the retracted position toward the driven position, which causes the hard tubular portion 50 and the adjacent segment of the soft tubular portion 48 to be moved into contact with the contoured surface of the forming body 72. The interaction between the hard tubular portion 50 and soft tubular portion 48 with the forming body 72 shapes the hard tubular portion 50 and the soft tubular portion 48 into a desired contour. For instance, an outer diameter of the catheter 12 may decrease toward the distal end defined by the hardened distal tip. Furthermore, the hard tubular portion 50 may define an internal shoulder 74.

Figure 6:
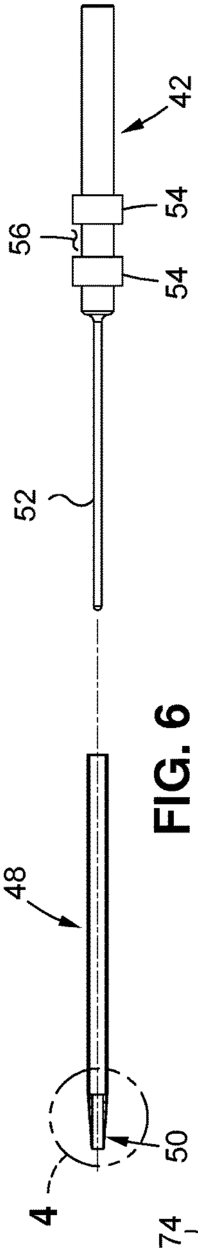
FIG. 6 is an exploded view of a shaped catheter segment and the mandrel used to shape the catheter segment.

The finished catheter forming process may be facilitated by activating a finger operated optical switch on a tipping machine (not pictured). Such activation may begin two processes. First, the mold cavity/die 72 may be heated to a preselected temperature via an RF cable (temperature controlled by a thermocouple, all of which may be contained inside the mold assembly). Second, the mandrel cradle 44 may be pneumatically pressed into the mold cavity/die 72, from right to left in the perspective depicted in FIG. 5, at an operator preselected pressure. Inside the heated mold cavity, the two assembled polyurethane catheter tubes 48, 50 may begin to melt, fusing the two overlapping catheter tubes 48, 50 together. The melted polyurethane catheter material conforms to the shape of the mold cavity/die 72, resulting in the designed tip geometry as depicted in FIGS. 6, 7). Any excess melted polyurethane catheter material may be "trimmed/cut" by the front tip of the mandrel making contact with the inside taper of the mold cavity/die 72. That excess polyurethane which gets cut off may be "ejected" out the rear of the mold cavity/mold assembly (e.g., to the left side of FIG. 5). Pneumatic air may be blown into the mold assembly, cooling and solidifying the polyurethane catheter tubing to the designed geometry. Finally, the mandrel cradle 44 may be pneumatically removed from the mold assembly (from left to right in FIG. 5), at which point the catheter tube may be formed as one continuous, integral part, and the operator is able to remove the catheter from the mandrel for further processing/assembly.

After the desired shape has been attained, the main body 60 is transitioned from the driven position to the retracted position, which removes the elongate shaft 52 and catheter 12 from the forming body 72. The mandrel 42 may then be removed from the drive mechanism 44, and the formed catheter 12 may be removed from the elongate shaft 52.

Referring now to FIGS. 8-14, there is depicted a system for assembling the catheter 12 to a ferrule 80 using a mandrel 82 and a pressing machine 84 to press the ferrule 80 into the catheter 12.

The ferrule 80 may be configured to facilitate engagement between the catheter 12 and the hub 22, as will be explained in more detail below. According to one embodiment, the ferrule 80 includes a wide portion 86 and a narrow portion 88. The wide portion 86 may be frustoconical, while the narrow portion 88 may be cylindrically tubular. The ferrule 80 may be formed of a metallic material that may be compressible or deformable in response to a prescribed force being applied thereto.

The mandrel 82 may include a base 90, a magnet 92, and a core pin 94. The base 90 may be in the shape of a disc, having a first surface 96 and an opposing second surface 98. The base 90 may additionally include a pair of side surfaces 100 extending between the first and second surfaces 96, 98 in spaced relation to each other to define an outer, circumferential groove extending around the base 90 between a pair of circumferential ribs. A recess 104 or opening may extend from the first surface 96 toward the second surface 98 along an axis 106 perpendicular to the first surface 96. The recess 104 may be centrally located on the base 90. The magnet 92 may be located within the base 90, adjacent one end of the recess 104, to facilitate magnetic engagement between the base 90 and the core pin 94. The magnet 92 may be secured to the base 90 via magnetic attraction, the use of adhesives, friction force, or through the use of other securing techniques known in the art.

The core pin 94 includes a wide portion 108 configured to be received within the recess 104 formed in the base 90, and a narrow portion 110 extending from the wide portion 108. The outer diameter of the wide portion 108 is slightly less than the inner diameter of the recess 104 to allow for easy placement of the wide portion 108 within the recess 104, while at the same time being large enough to prevent tipping of the core pin 94 while seated in the base 90. The outer diameter of the wide portion 108 may also be slightly less than a maximum outer diameter of the wide portion 86 of the ferrule 80 to allow an end of the wide portion 108 of the core pin 94 to be received within the wide portion 86 of the ferrule 80. The narrow portion 110 is configured to be received within the narrow portion 88 of the ferrule 80 as well as the soft portion 48 of the catheter 12.

During use, the ferrule 80 is loaded on the core pin 94, with the wide portion 86 of the ferrule 80 being advanced over the narrow portion 110 of the core pin 94. The ferrule 80 is moved over the narrow portion 110 of the core pin 94 until the wide portion 86 of the ferrule 80 is seated against the wide portion 108 of the core pin 94. The open end of the soft portion 48 of the catheter 12 (i.e., the end opposite the hard tip) is placed onto the narrow portion 110 of the core pin 94 and is moved over the core pin 94 until the catheter 12 rests against the narrow portion 88 of the ferrule 80.

Figures 8, 9, 10, 11:
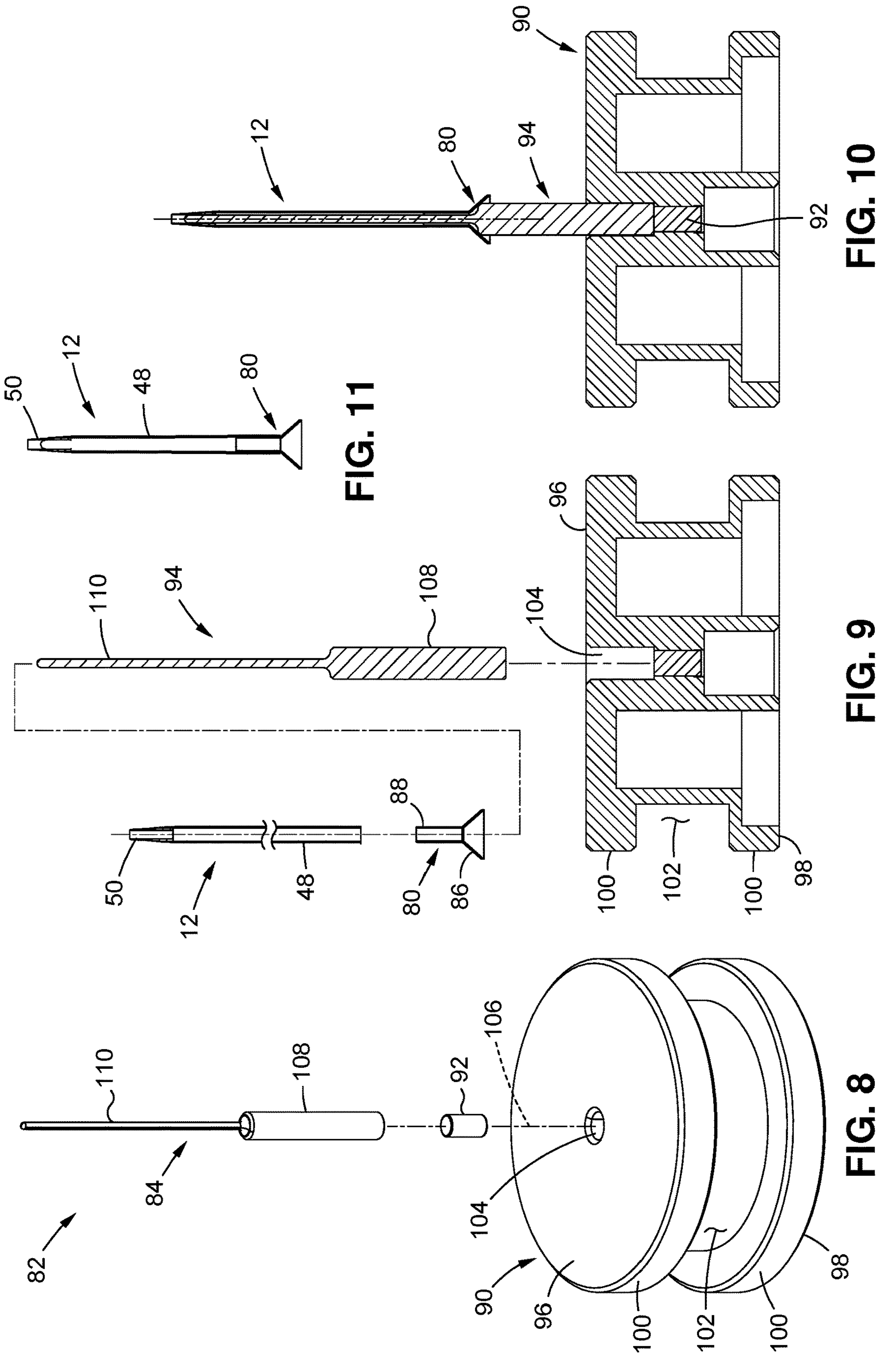
FIG. 8 is an exploded upper perspective view of a pressing mandrel including a base, a magnet, and a core pin.
FIG. 9 is a cross sectional view of a shaped catheter, a ferrule, the core pin, and the base having the magnet connected thereto.
FIG. 10 is an assembled cross sectional view of the shaped catheter, the ferrule, the core pin, and the base having the magnet connected thereto, with the assembly being ready for pressing the ferrule into the shaped catheter.
FIG. 11 is a cross sectional view of the ferrule inserted into the shaped catheter.

The wide portion 108 of the core pin 94 is placed within the recess 104, either before or after loading of the ferrule 80 and catheter 12 thereon, such that the base 90, the ferrule 80, and the catheter 12 assume the configuration shown in FIG. 10, and is ready for placement on the pressing machine 84. When the wide portion 108 of the core pin 94 is placed in the base 90, the wide portion 108 may be magnetically attracted to the magnet to urge the core pin 94 into its seated position within the base 90. The core pin 94 may remain in this position during the pressing operation, and then be removed from the base 90 after the pressing operation, as will be explained in more detail below.

Figure 12:
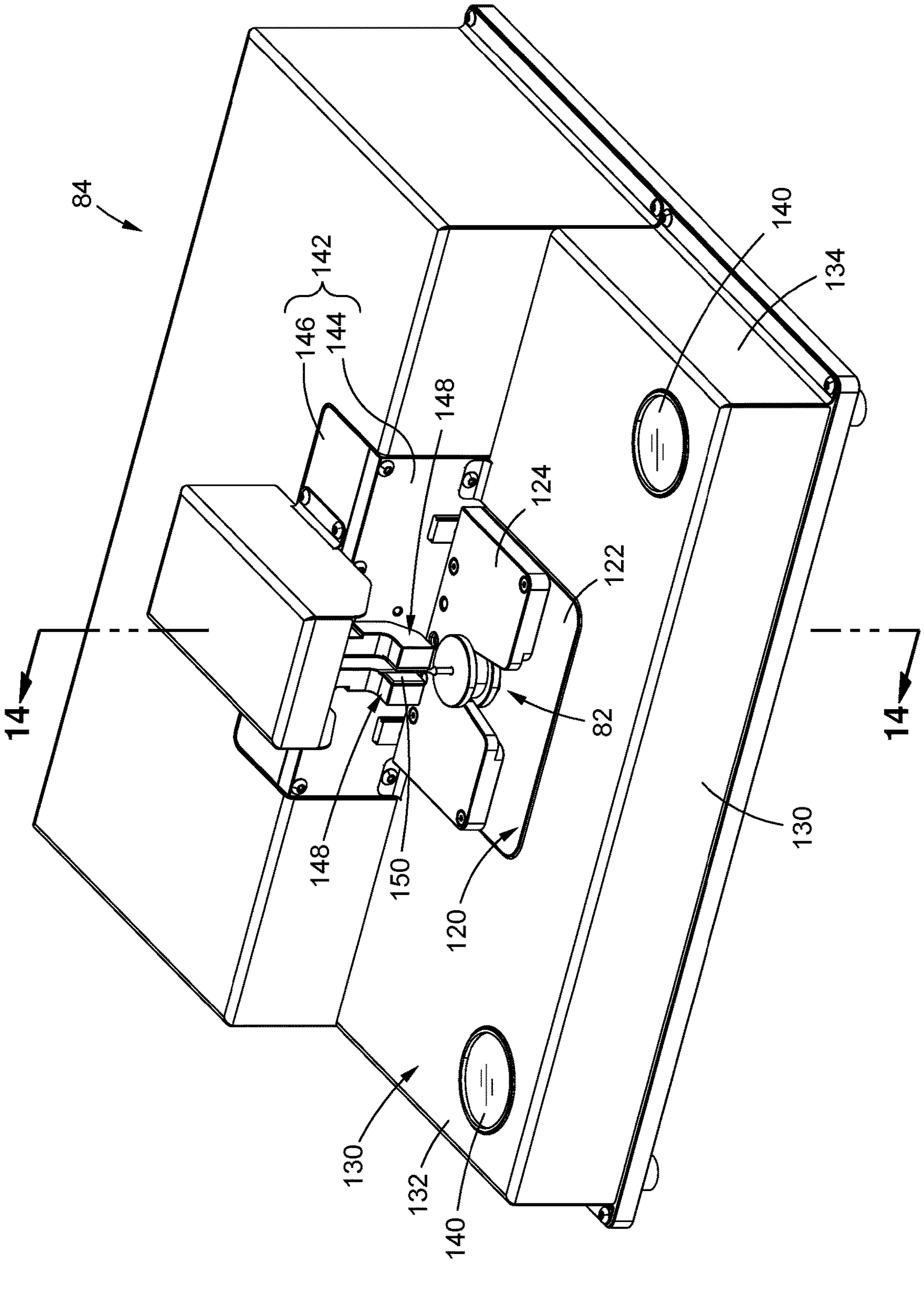
FIG. 12 is an upper perspective view of a pressing machine and the pressing mandrel in use on the pressing machine.
Figure 13:
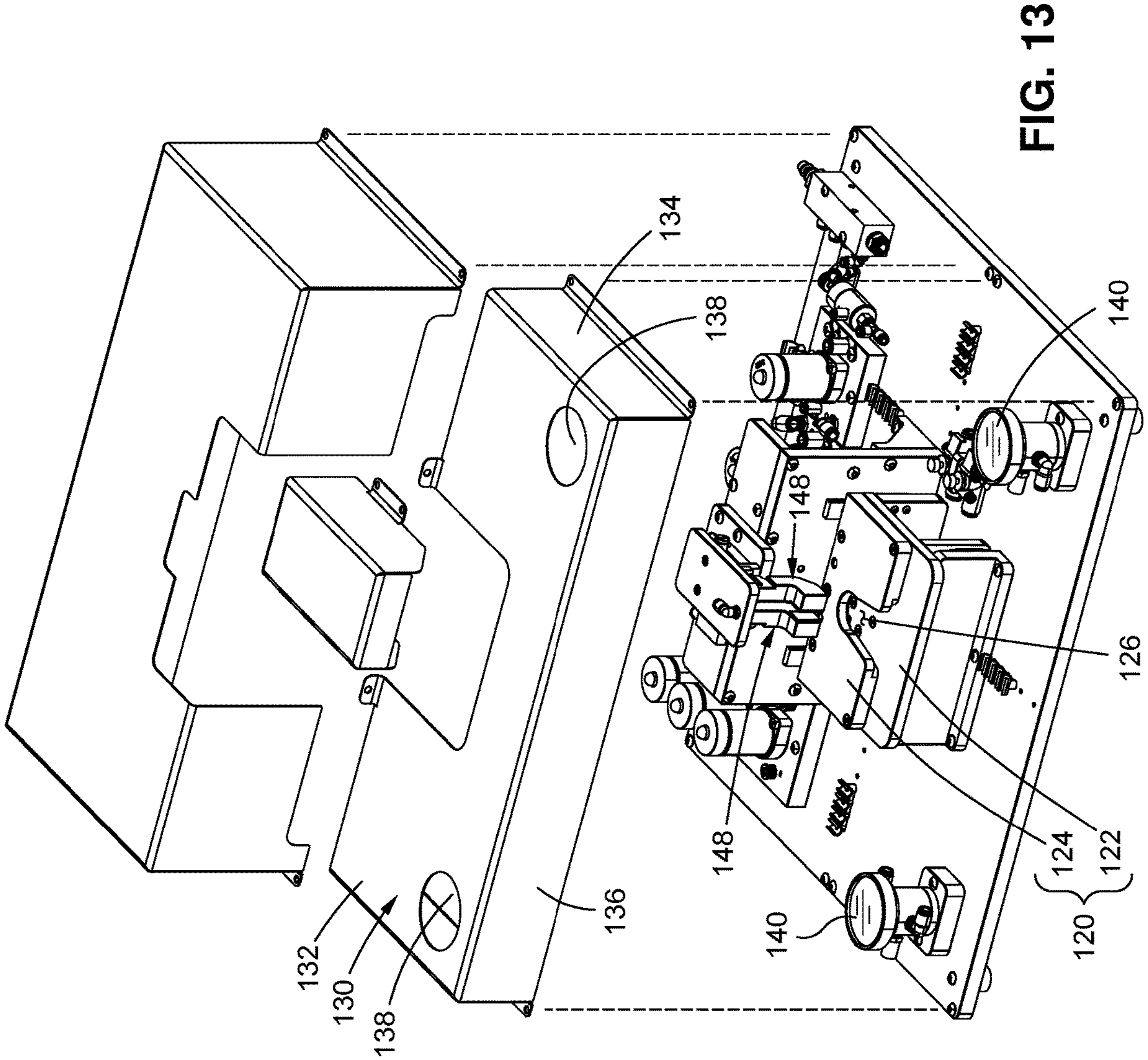
FIG. 13 is an exploded, upper perspective view of the pressing machine.
Figure 14:
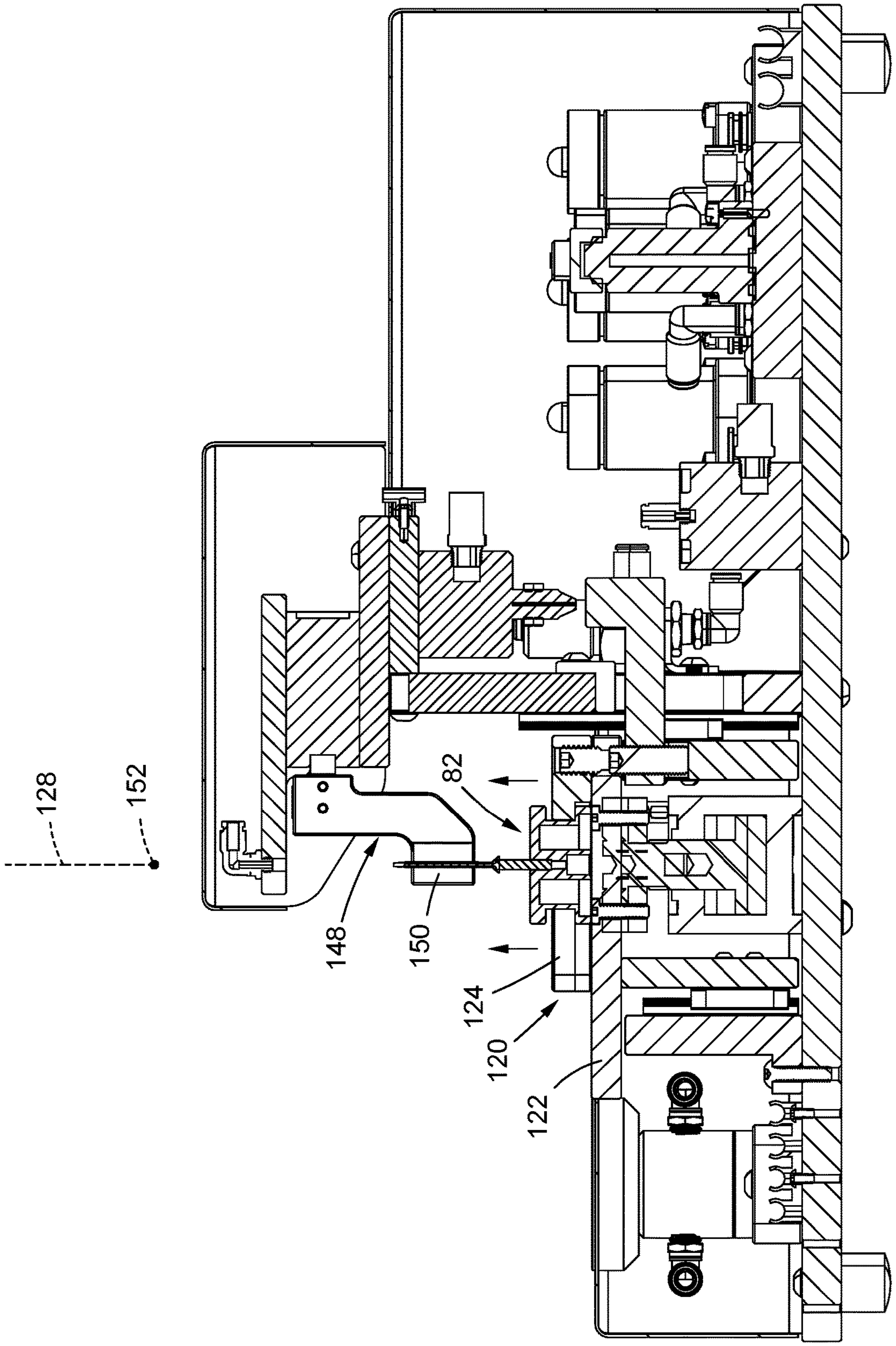
FIG. 14 is a side, cross sectional view of the pressing machine.
Figure 15:
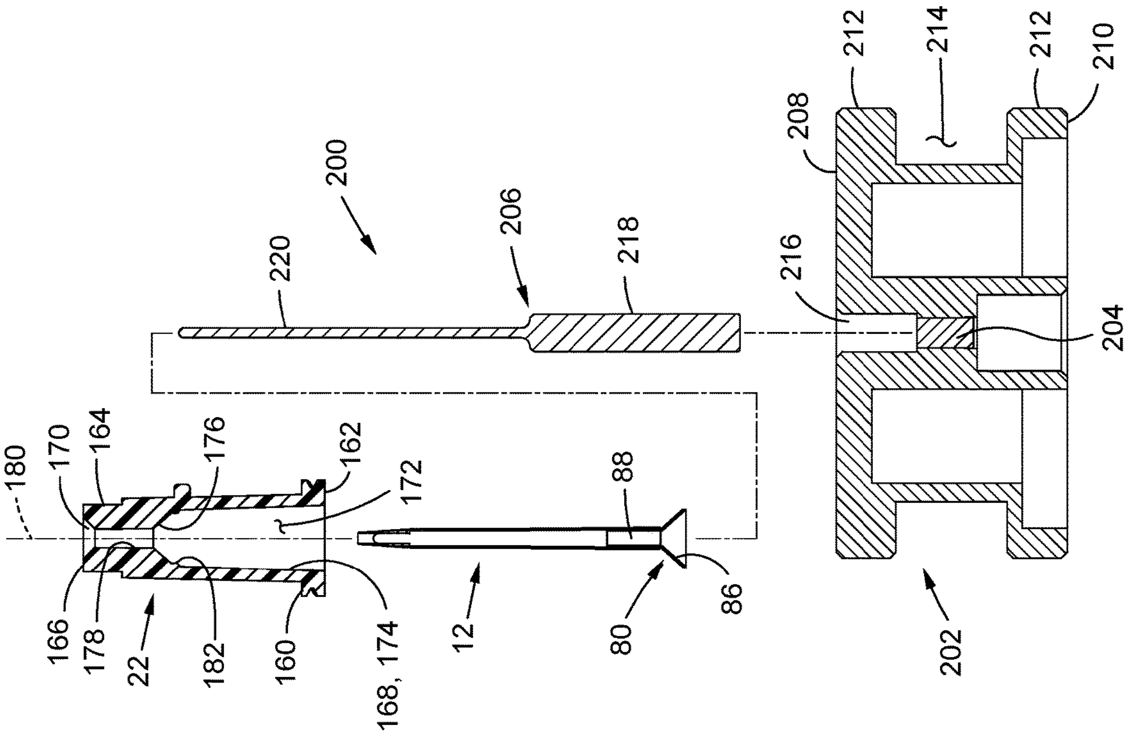
FIG. 15 is a cross sectional view of a hub, shaped catheter, a ferrule, the core pin, and the base having the magnet connected thereto.
Figure 16:
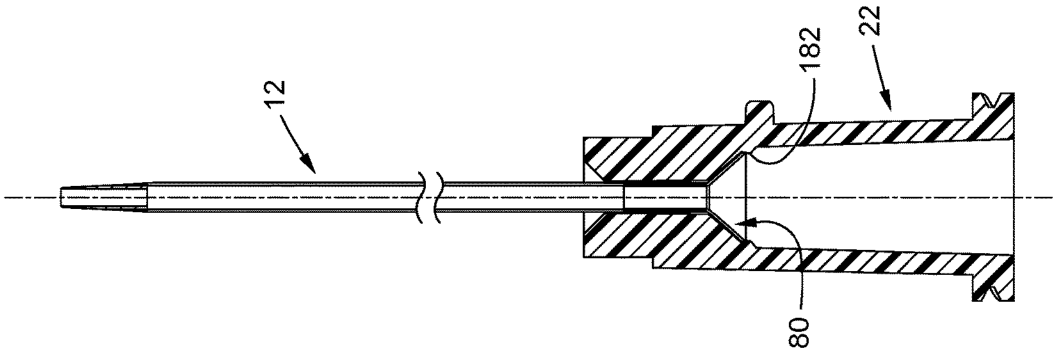
FIG. 16 is a cross sectional view of the hub connected to the shaped catheter using the ferrule.

FIG. 12 shows an exemplary embodiment of the pressing machine 84 used to press the ferrule 80 into the soft catheter 12 while on the mandrel 82. The pressing machine 84 may include a rising assembly 120 including a lower press plate 122 and a press flange 124 extending generally parallel to the lower press plate 122 in spaced relation thereto. The press flange 124 may include an outer periphery that forms a recess 126 (see FIG. 13) extending from an outermost edge, with the recess 126 having a rounded end portion being similar in configuration to that of the base 90. The space between the press flange 124 and the lower press plate 122 may define a gap having a thickness that corresponds to the thickness of a circumferential rib on the base 90 of the mandrel 82. Thus, the rising assembly 120 may be configured to engage with the mandrel 82 with one rib of the base 90 extending between the press flange 124 and the lower press plate 122, and the press flange 124 being received within a portion of the circumferential groove 102 formed on the mandrel 82.

The rising assembly 120 may be selectively transitional between a raised position and a lowered position, with the rising assembly 120 moving along a pressing axis 128 generally perpendicular to an outer surface of the lower press plate 122 as the rising assembly 120 transitions between the raised position and the lowered position.

Surrounding the lower press plate 122 on three sides is a lower housing 130, which may include an upper surface 132, a pair of side surfaces 134, and a front surface 136. A pair of openings 138 may be formed adjacent respective corners of the upper surface 132, with each opening 138 accommodating a respective manually actuating button 140, which when concurrently depressed, may generate a signal which may facilitate a reciprocal, lifting and falling motion of the rising assembly 120 relative to the lower housing 130.

The pressing machine 84 may additionally include a fixed body 142 positioned adjacent the rising assembly 120 and having a vertical wall 144 and a horizontal wall 146. Mounted to the fixed body 142 are a pair of arms 148, with each arm 148 including an inner gripping surface 150. The pair of arms 148 may be arranged with the inner gripping surfaces 150 in opposed relation to each other. The arms 148 are configured to be transitional between a release position and a gripping position, with the arms 148 moving toward each other as they transition from the release position toward the gripping position, and moving away from each other as the transition from the gripping position toward the release position. The arms 148 may hold the catheter 12 in place when the arms 148 are in the gripping position and while the ferrule 80 is urged into the catheter 12 to facilitate insertion of the ferrule 80 into the catheter 12. According to one embodiment, the arms 148 move along a gripping axis 152 that is generally perpendicular to the pressing axis 128 as the arms 148 transition between the gripping position and the release position.

In one embodiment, the pressing machine 84 may require concurrent pressing to actuate the pressing functionality. The pressing machine 84 may be a pneumatic machine, wherein the movement associated with the pressing functionality may be controlled via pneumatic signals. However, it is contemplated that electric signals and electronic components (e.g., a motor, etc.) may be used in the pressing machine 84 without departing from the spirit and scope of the present disclosure.

During use of the pressing machine 84, the mandrel, with the ferrule 80 and shaped catheter 12 loaded thereon, is placed on the pressing machine 84. In particular, the lower surface of the base 90 is placed on the lower press plate 122, and is moved into the recess defined by the press flange 124, with the press flange 124 being received within the circumferential groove of the mandrel, and a circumferential rib of the mandrel is received between the lower press plate 122 and the press flange 124. The lower press plate 122 may include a magnet coupled thereto, which may be magnetically attracted to the magnet in the base 90 when the mandrel is in proper position on the lower press plate 122.

When the mandrel 82 is in place, an operator of the pressing machine 84 may simultaneously press on the actuator buttons 140, which causes a pneumatic signal to move the arms 148 and the rising assembly 120. In particular, the arms 148 may be moved slightly before the rising assembly 120, with the arms 148 transitioning from their release position to their gripping position, to apply a gripping force on the catheter 12. In this regard, the forces applied on the catheter 12 by the arms 148 are in opposed relation to each other on opposed points or regions of the catheter 12.

While the arms 148 are in the gripping position, the rising assembly 120 is transitioned from the lowered position to the raised position, which causes movement of the mandrel 82 relative to the catheter 12. In particular, the catheter 12 is held in place by the gripping force applied by the arms 148. Furthermore, transition of the rising assembly 120 from the lowered position to the raised position, while the catheter 12 is held in place, causes relative movement between the ferrule 80 and the catheter 12. In particular, as the rising assembly 120 moves from the lowered position to the raised position, the ferrule 80, moving with the rising assembly 120, is advanced into the catheter 12, which does not move with the rising assembly 120, due to the gripping force applied by the arms 148. When the rising assembly 120 reaches the raised position, the ferrule 80 may be completely advanced into the catheter 12 and a friction force between the ferrule 80 and the catheter 12 may hold the ferrule 80 within the catheter 12 in the advanced position. In this regard, resiliency in the catheter 12 may cause the catheter 12 to slightly expand in diameter to accommodate the ferrule 80, while also imparting a circumferential frictional force on the ferrule 80.

Once the ferrule 80 is completely advanced into the catheter 12, the arms 148 may transition from the gripping position to the release position, and the rising assembly 120 may transition from the raised position to the lowered position.

Referring now to FIGS. 15-18, the ferrule 80, after having been attached to the catheter 12, may then be used for attachment to a hub 22 with the use of a mandrel 200 and pressing machine 230. The hub 22 may include a proximal end portion 160 having a proximal end face 162 and a distal end portion 164 having a distal end face 166. An inner surface 168 may extend through the hub 22 between the proximal end face 162 and the distal end face 166 and around a central axis 180 to define an opening 172 through the hub 22. The diameter of the inner surface may vary between the proximal end face 162 and the distal end face 166 to define a slightly tapered proximal region 174, a more significantly tapered first intermediate region 176, a generally cylindrical second intermediate region 178 and a tapered distal region 170. The proximal region 174 and the first intermediate region 176 may be separated by a protruding circumferential rib 182 having a diameter less than the adjacent sections of the proximal region 174 and the first intermediate region 176.

Attachment of the ferrule 80 to the hub 22 may include the use of a mandrel 200, similar to the mandrel 42 discussed above, with the mandrel 200 including a base 202, a magnet 204, and a core pin 206. The base 202 may be in the shape of a disc, having a first surface 208 and an opposing second surface 210. The base 202 may additionally include a pair of side surfaces 212 extending between the first and second surfaces 208, 210 in spaced relation to each other to define an outer, circumferential groove 214 extending around the base 202 between a pair of circumferential ribs. A recess 216 or opening may extend from the first surface 208 toward the second surface 210 along an axis perpendicular to the first surface 208. The recess 216 may be centrally located on the base 202. The magnet 204 may be located within the base 202, adjacent one end of the recess 216, to facilitate magnetic engagement between the base 202 and the core pin 206. The magnet 204 may be secured to the base 202 via magnetic attraction, the use of adhesives, friction force, or through the use of other securing techniques known in the art.

The core pin 206 includes a wide portion 218 configured to be received within the recess 216 formed in the base 202, and a narrow portion 220 extending from the wide portion 218. The outer diameter of the wide portion 218 is slightly less than the inner diameter of the recess 216 to allow for easy placement of the wide portion 218 within the recess 216, while at the same time being large enough to prevent tipping of the core pin 206 while seated in the base 202. The outer diameter of the wide portion 218 may also be slightly less than a maximum outer diameter of the wide portion of the ferrule 80 to allow an end of the wide portion 218 of the core pin 206 to be received within the wide portion 86 of the ferrule 80. The narrow portion 220 of the core pin 206 is configured to be received within the narrow portion 88 of the ferrule 80 as well as the soft portion 48 of the catheter 12.

During use, the ferrule 80 and catheter 12 are loaded on the core pin 206, with the wide portion 86 of the ferrule 80 being advanced over the narrow portion 220 of the core pin 206. The ferrule 80 is moved over the narrow portion 220 of the core pin 206 until the wide portion 86 of the ferrule 80 is seated against the wide portion 218 of the core pin 206 and the catheter 12 extends over the narrow portion 220 of the core pin 206.

The hub 22 may be placed over the catheter 12, with the proximal end portion 160 of the hub 22 being placed over the catheter 12. The hub 22 is moved over the catheter 12 and core pin 206 with the catheter 12 and core pin 206 advancing through the opening 172 in the hub 22. The maximum outer diameter of the ferrule 80 may be slightly larger than the inner diameter of the circumferential rib 182 extending into the hub opening 172, and thus, the advancement of the hub 22 over the catheter 12 may be stopped by abutment of the circumferential rib 182 and the wide portion 86 of the ferrule 80.

The wide portion 218 of the core pin 206 is placed within the recess 216 on the base 202, either before or after loading of the hub 22, ferrule 80, and catheter 12 thereon. When the wide portion 218 is placed in the base 202, the wide portion 218 may be magnetically attracted to the magnet 204 to urge the core pin 206 into its seated position within the base 202. The core pin 206 may remain in this position during the pressing operation, and then be removed from the base 202 upon completion of the pressing operation, as will be explained in more detail below. When the core pin 206 is placed within the recess, with the hub 22, ferrule 80, and catheter 12 loaded thereon, the proximal end face of the hub 22 may be spaced from the base 202, due to the hub 22 resting on the circumferential rib 182. At this point, the loaded mandrel 200 is ready for placement on the pressing machine 230.

Figure 17:
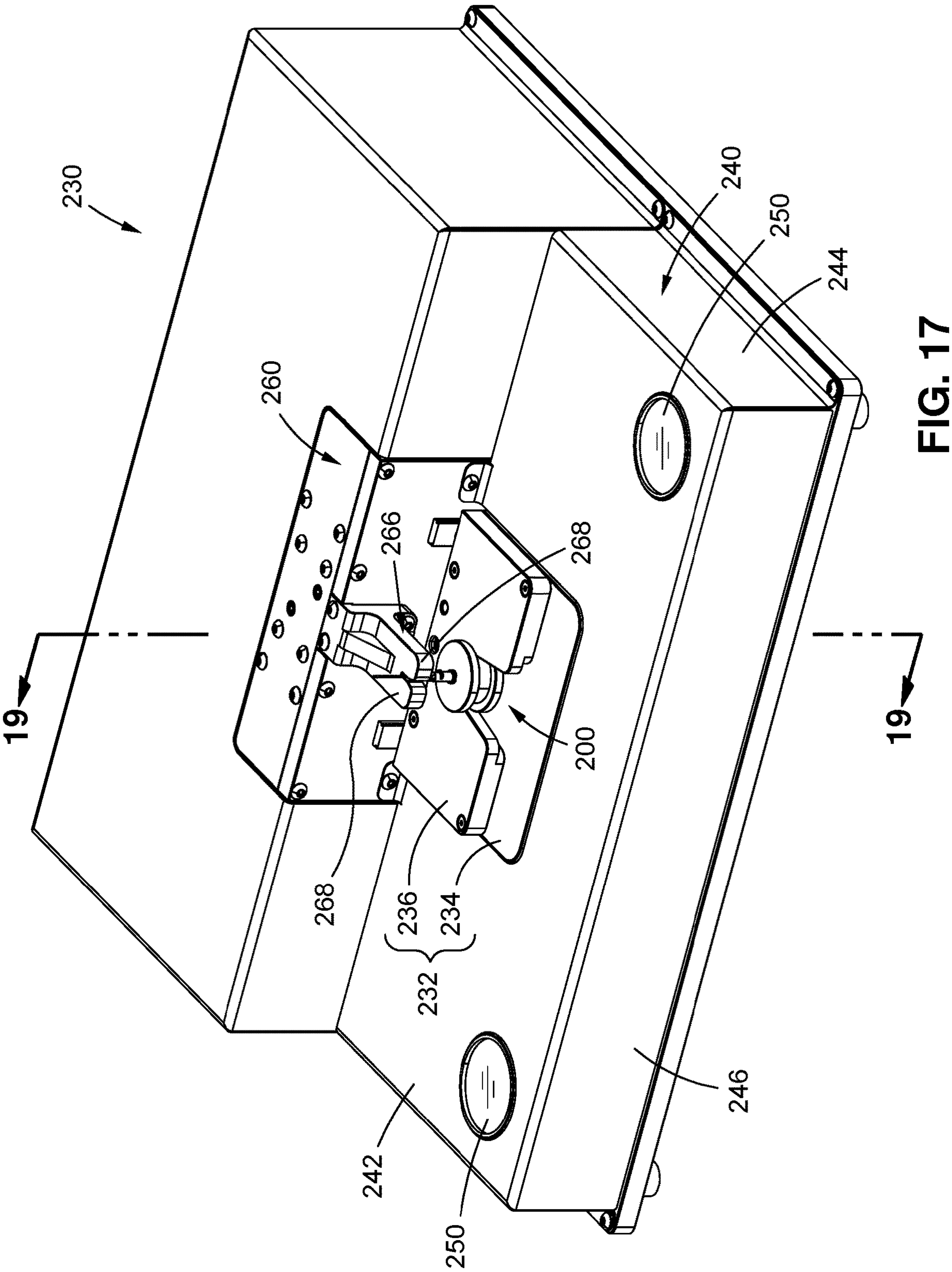
FIG. 17 is an upper perspective view of a pressing machine used to press the hub onto the catheter, and the pressing mandrel in use on the pressing machine.
Figure 18:
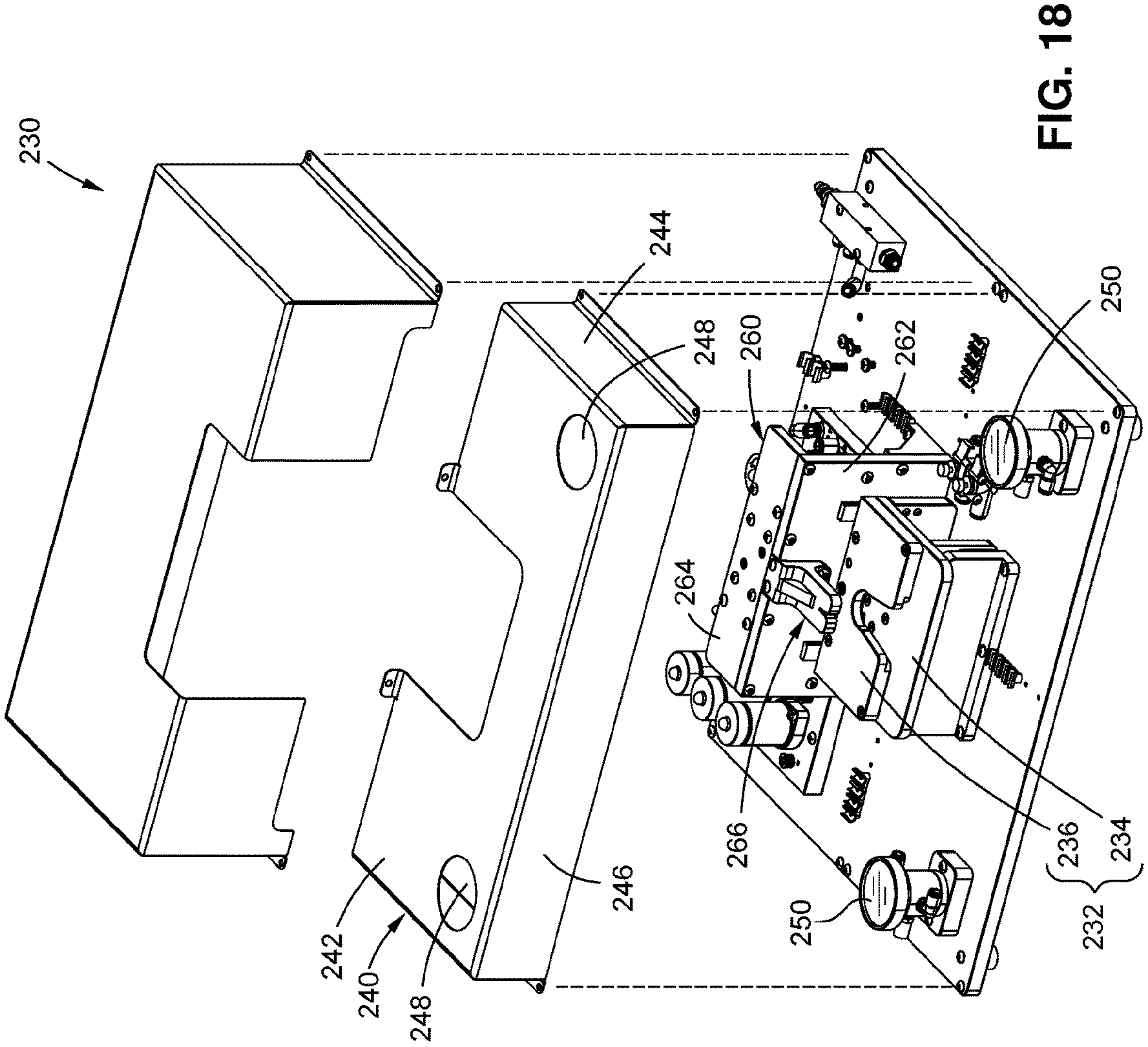
FIG. 18 is an exploded, upper perspective view of the pressing machine depicted in FIG. 17.

FIGS. 17 and 18 shows an exemplary embodiment of the pressing machine 230 used to press the ferrule 80 into the soft catheter 12 while on the mandrel 200. The pressing machine 230 may include a rising assembly 232 including a lower press plate 234 and a press flange 236 extending generally parallel to the lower press plate 234 in spaced relation thereto. The press flange 236 may include an outer periphery that forms a recess extending from an outermost edge, with the recess having a rounded end portion similar in size to the base 202. The space between the press flange 236 and the lower press plate 234 may define a gap having a thickness that corresponds to the thickness of a circumferential rib on the base 202 of the mandrel 200. Thus, the rising assembly 232 may be configured to engage with the mandrel 200 with one rib extending between the press flange 236 and the lower press plate 234, and the press flange 236 being received within a portion of the circumferential groove 214 formed on the mandrel 200.

The rising assembly 232 may be selectively transitional between a raised position and a lowered position, with the rising assembly 232 moving along a pressing axis 238 generally perpendicular to an outer surface of the lower press plate 234 as the rising assembly 232 transitions between the raised position and the lowered position.

Surrounding the lower press plate 234 on three sides is a lower housing 240, which may include an upper surface 242, a pair of side surfaces 244, and a front surface 246. A pair of openings 248 may be formed adjacent respective corners of the upper surface 242, with each opening 248 accommodating a respective manual actuating button 250, which when concurrently depressed, may generate a signal which may facilitate a reciprocal, lifting and falling motion of the rising assembly 232 relative to the lower housing 240.

The pressing machine 230 may additionally include a fixed body 260 positioned adjacent the rising assembly 232 and having a vertical wall 262, a horizontal wall 264, and a fork 266 connected to the horizontal wall 264. The fork 266 may include a pair of fingers 268 that are separated by a recess that is aligned with the recess in the press flange 236.

With regard to actuation of the pressing machine 230, one embodiment thereof may be configured to require concurrent pressing of the buttons 250 to actuate the pressing functionality. The pressing machine 230 may be a pneumatic machine, wherein the movement associated with the pressing functionality may be controlled via pneumatic signals. However, it is contemplated that electric signals and electronic components (e.g., a motor, etc.) may be used in the pressing machine 230 without departing from the spirit and scope of the present disclosure.

During use of the pressing machine 230, the mandrel 200, with the hub 22, ferrule 80 and catheter 12 loaded thereon, is placed on the pressing machine 230. In particular, the lower surface 210 of the base 202 is placed on the lower press plate 234, and is moved into the recess defined by the press flange 236, with the press flange 236 being received within the circumferential groove 214 of the mandrel 200, and a circumferential rib of the mandrel 200 is received between the lower press plate 234 and the press flange 236. The lower press plate 234 may include a magnet coupled thereto, which may be magnetically attracted to the magnet 204 in the base 202 when the mandrel 200 is in proper position on the lower press plate 234.

When the mandrel 200 is in place, an operator of the pressing machine 230 may simultaneously press on the actuator buttons 250, which causes a pneumatic signal to move the rising assembly 232. The rising assembly 232 is transitioned from the lowered position to the raised position, which causes the hub 22 to be moved toward the fork 266. Eventually, the hub 22 will contact the fork 266 to limit further upward movement of the hub 22. However, the lower press plate 234 may continue to rise, thus, moving the proximal end face of the hub 22 toward the mandrel 200. Such movement may cause the circumferential rib 182 of the hub 22 to move over the end of the ferrule 80, thereby causing the tapered portion of the ferrule 80 to be captured within the first intermediate portion 176 of the opening 172 in the hub 22. Subsequently, the rising assembly 232 may transition from the raised position to the lowered position, and the newly formed catheter-hub subassembly may be removed from the mandrel 200.

It is contemplated that glue may be used to seal and secure the attachment of the catheter 12 to the hub 22. In particular, one or more drops of adhesive may be placed in or near the distal end portion 164 of the hub 22 adjacent the protruding catheter 12.

In one embodiment, a liquid, ultraviolet (UV) cured adhesive may be applied in two places for the assembly of the catheter. One application may be on the catheter/hub subassembly. The fully formed and tipped catheter tube may be placed onto a metal ferrule 80. That catheter and ferrule may be then inserted into a color-coded hub (or a color-coded hub may be assembled over the catheter-ferrule subassembly). The front of the hub may include a small "well" feature (e.g., tapered distal region 170) through which the catheter tube protrudes. The UV cured liquid adhesive may be applied into this "well" via an adhesive dispensing machine. The purpose of the adhesive in this location may be to secure the catheter tube to the hub as well as provide a fluid tight seal to prevent any blood, medications, etc., from leaking though the hub assembly.

Figure 20:
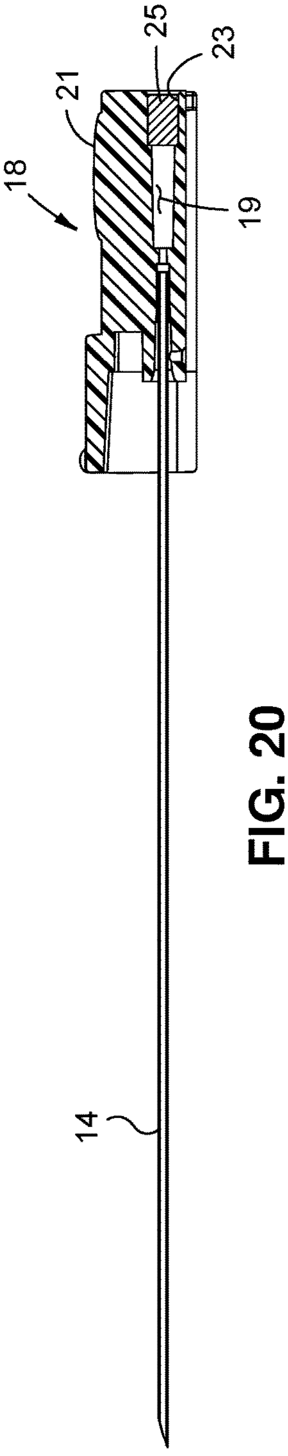
FIG. 20 is a side, cross sectional view of a slider connected to a needle and a vent plug.
Figure 21:
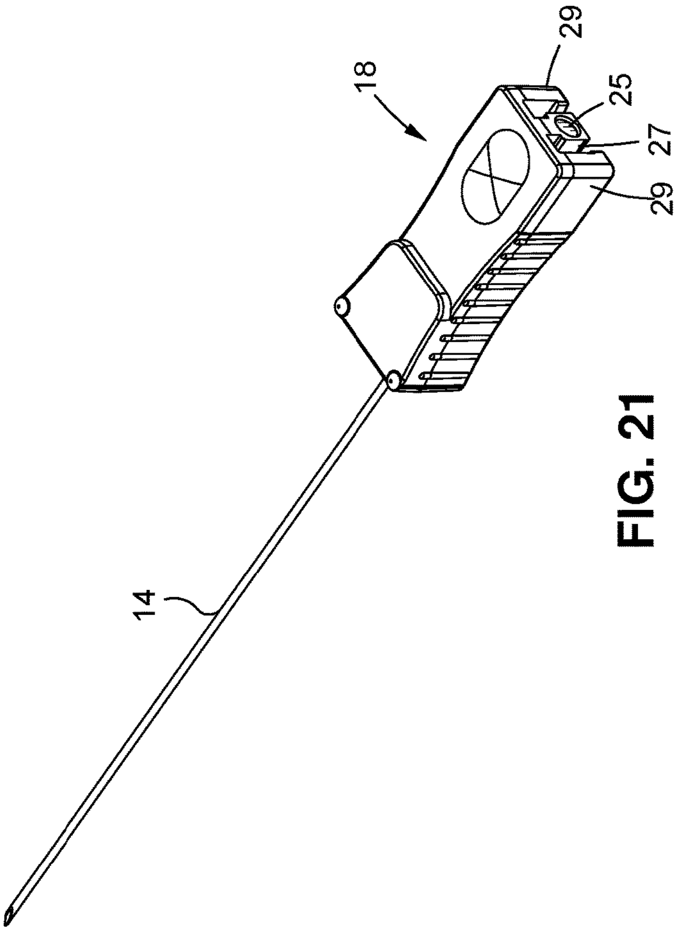
FIG. 21 is a lower perspective view of the slider connected to the needle.
Figure 22:
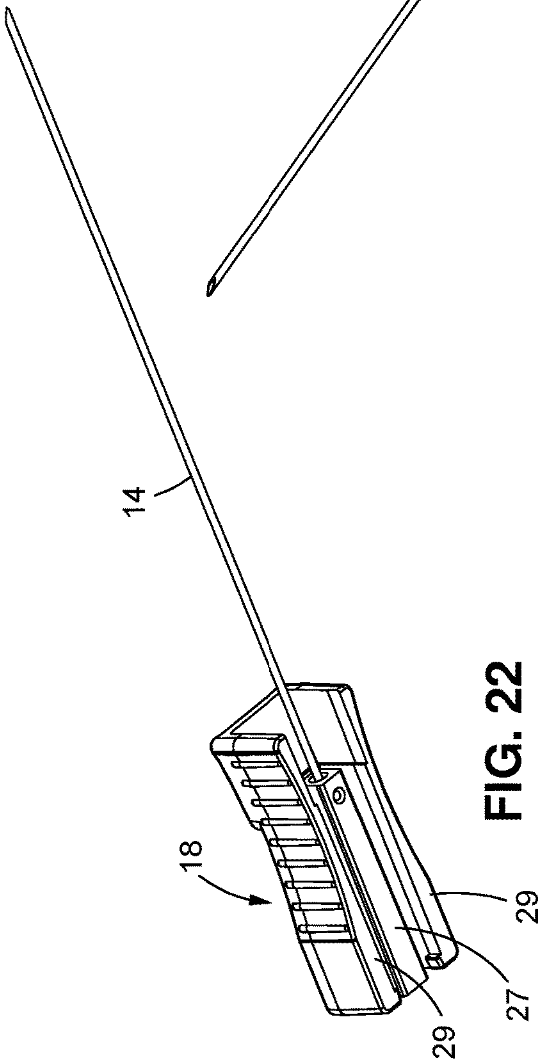
FIG. 22 is an upper perspective view of the slider, connected to the needle and the vent plug
Figure 24:
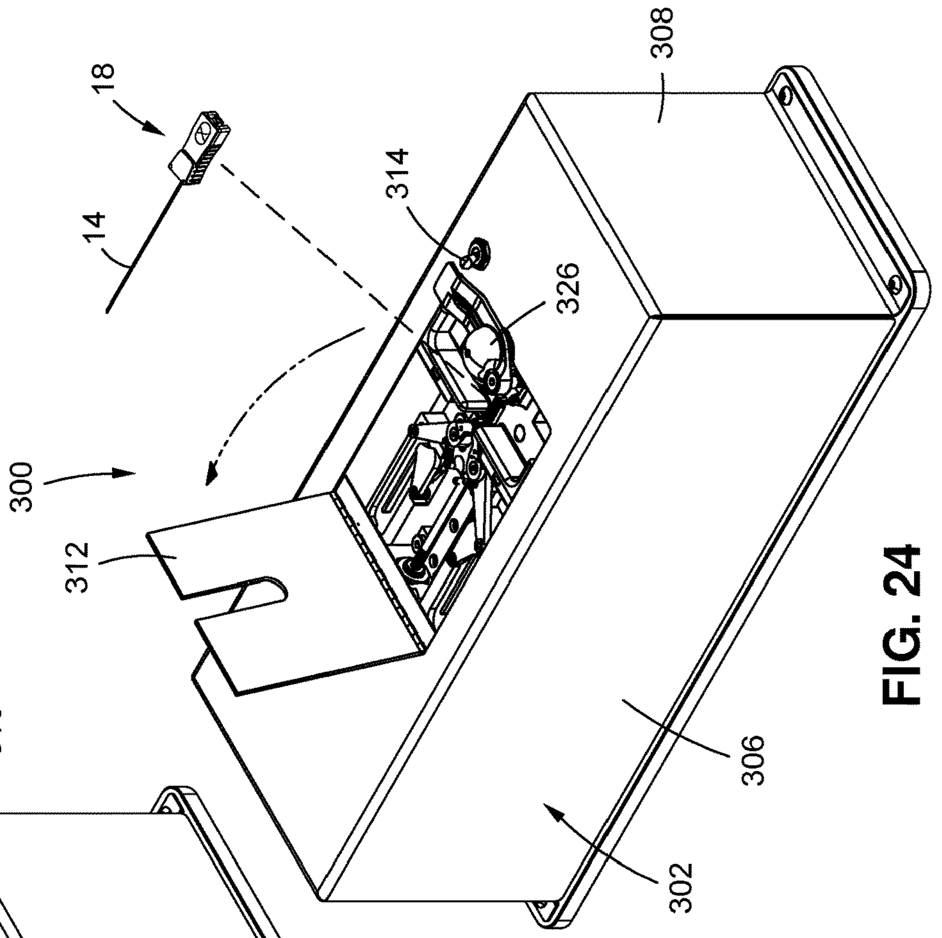
FIG. 24 is a front, upper perspective view of the device of FIG. 23, with a slider, connected to a needle and exploded from the device.
Figure 23:
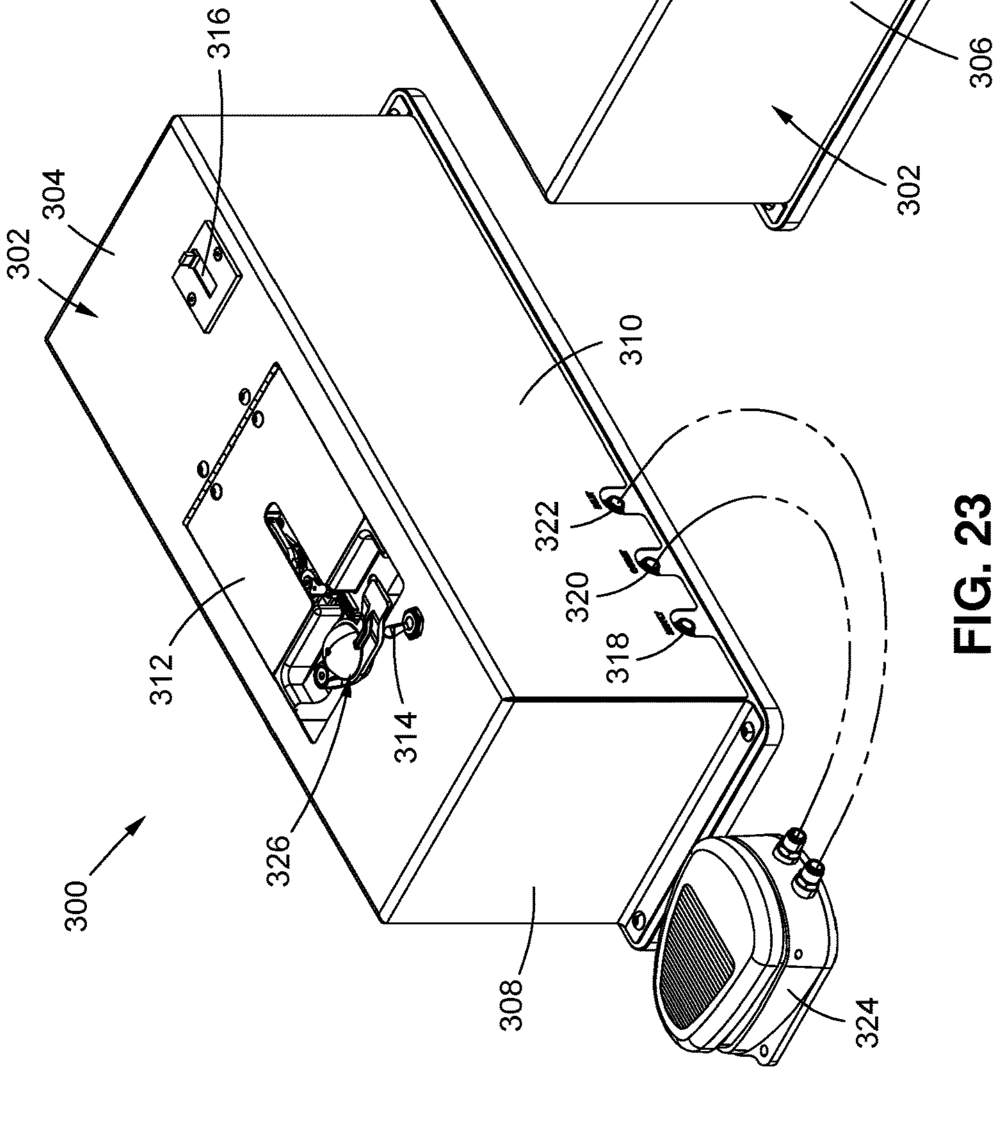
FIG. 23 is a rear, upper perspective view of a device for inserting the vent plug into the slider and wiping the needle with a lubricant.
Figure 25:
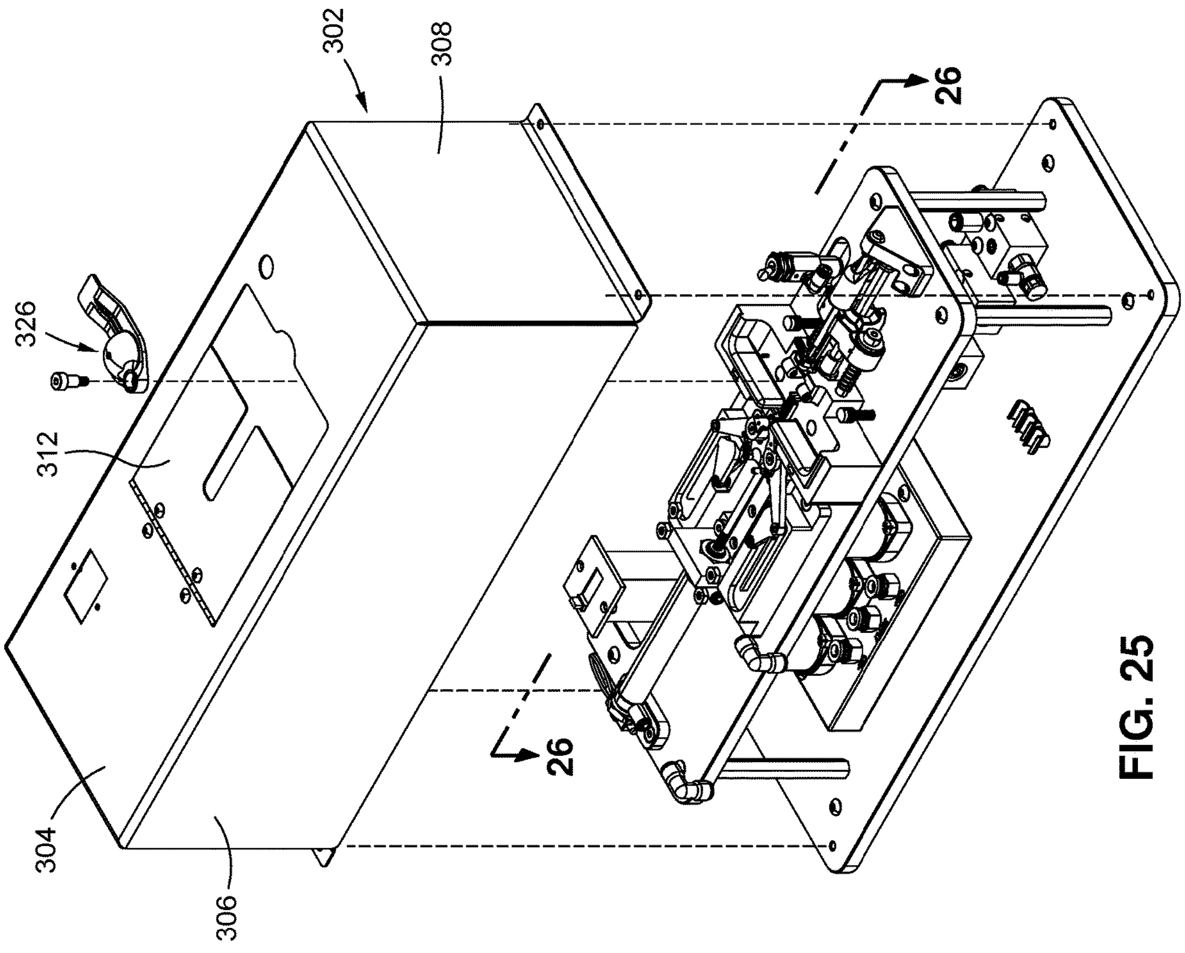
FIG. 25 is a front, exploded view of the device depicted in FIG. 23.

The second adhesive application may be on the needle-flash chamber subassembly (e.g., FIGS. 20, 21 and 22). The rear of the needle-blunt cannula assembly 14 may be inserted into the front of the slider/flash trap 18 leaving the needle bevel/sharp exposed. To secure the needle-blunt cannula to the flash trap 18 and provide a fluid tight seal, adhesive may be applied through a hole located in the bottom of the flash trap 18. This hole may allow an adhesive dispenser to apply adhesive into the hole; the adhesive can then migrate down to the needle-blunt cannula and wick around the outside of the blunt cannula, filling the cavity and securing and sealing the two parts.

As noted above, the universal passive protector 10 includes a hypodermic needle 14 that is connected to a slider 18. The slider 18 includes a flashback chamber 19 formed therein and in fluid communication with the needle 14 to allow blood or other bodily fluid that passes through the needle 14 to flow into the flashback chamber 19. A portion of a slider upper surface 21 may include a transparent section that is in alignment with the flashback chamber 19 to allow a user to view into the flashback chamber 19 through the transparent section. In one embodiment, the flashback chamber 19 is located in a lower portion of the slider 18 (e.g., below the upper surface 21). The slider 18 may also include a flashback inlet connectable to the needle 14 and configured to form a fluid pathway between the needle 14 and the flashback chamber 19 when the needle 14 is connected to the flashback chamber 19. The slider 18 may further include a vent opening 23 in communication with the flashback chamber 19. A plug 25 is insertable within a vent opening 23 to prevent blood from exiting the flashback chamber 19. The plug 25 is preferably configured to allow gases to pass therethrough, while restricting the passage of liquids therethrough.

Referring now to FIGS. 23-28, there is depicted a device 300 for placing the plug 25 in the vent opening 23, as well as wiping the needle 14 with a lubricant. The device 300 generally includes a housing 302 having an upper surface 304, a front surface 306, a pair of side surfaces 308, and rear surface 310. A pair of attachment flanges extend from respective side surfaces to facilitate attachment of the housing 302 to a work bench or other supporting surface. The upper surface 304 may be pivotally coupled to a cover 312, which may be pivoted to selectively cover or uncover internal components of the device 300. The device 300 may additionally include a switch 314 and a window 316 coupled to, or extending through, the upper surface 304. The switch 314 may be an ON/OFF toggle switch that may be selectively positioned in the ON position when ready for use, and in the OFF position during periods of nonuse. As will be explained in more detail below, the device 300 may be pneumatically actuated, and thus, placing the switch 314 in the ON position may facilitate connection with a pressurized air source (or other pneumatic supply), and placing the switch 314 in the OFF position may facilitate disconnection or closure from the pressurized air source.

The window 316 may be aligned with a counter, which may keep track of how many times the device 300 has been used. The counter may be capable of being reset after a given period of time (e.g., after a given shift, after a given day, etc.) or continue counting without resetting.

Figure 19:
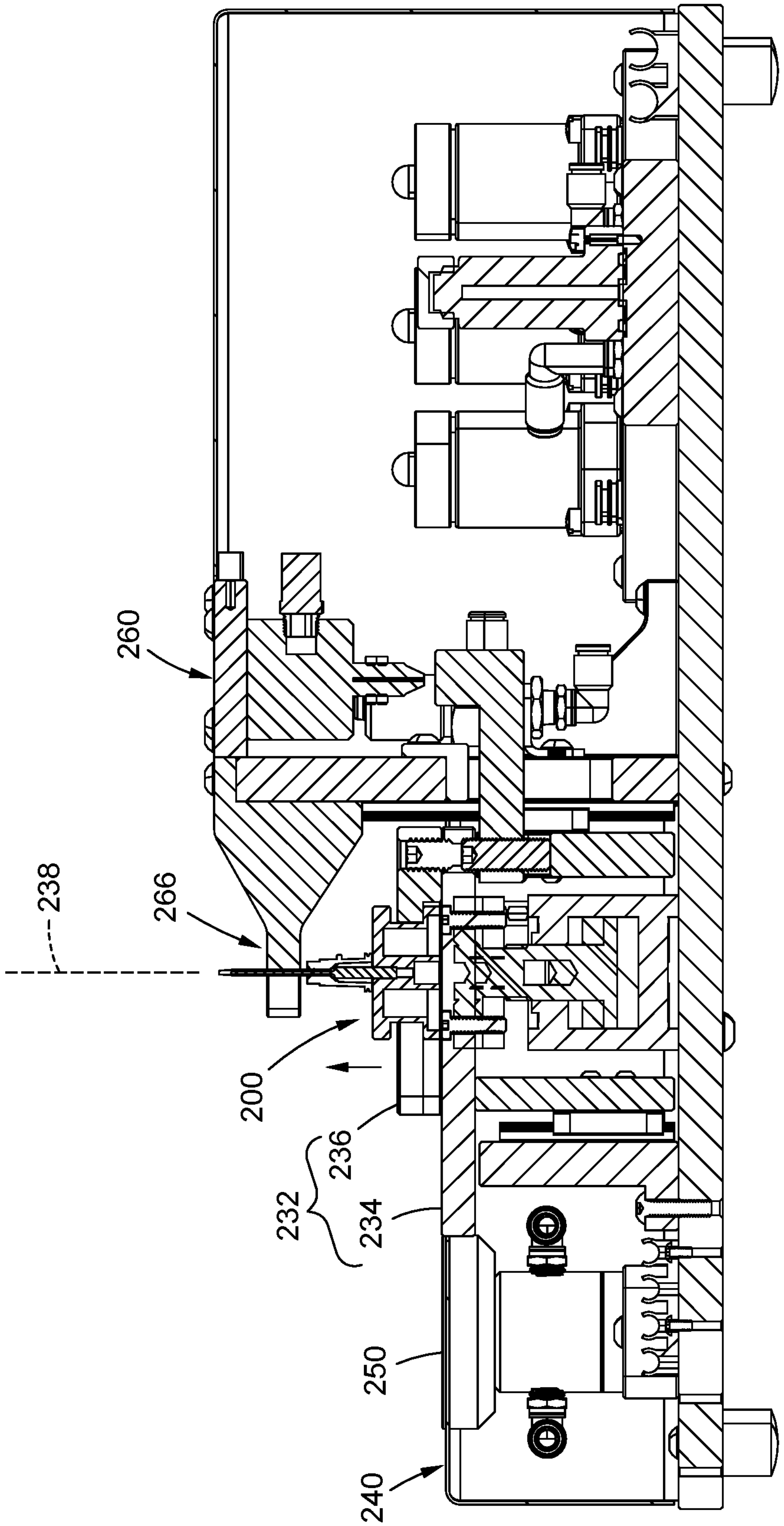
FIG. 19 is a side, cross sectional view of the pressing machine depicted in FIG. 17.

As noted above, the device 300 may be configured to be pneumatically operable, and thus, one or more pneumatic connections may be provided on the device 300. FIG. 19 shows the device 300 including a supply connection 318, an outlet connection 320, and an inlet connection 322. The connections 318, 320, 322 may be fluidly connected to a controller 324, such as a foot-actuated pedal, which when pressed, may facilitate transmission of a pneumatic signal.

One connection point 318 may be a main supply air inlet port. This connection may supply compressed air to the entire needle wipe down machine 300 from an air storage tank and/or an air compressor. Compressed air may directed from the compressed air storage tank into the machine main air inlet and out to a foot pedal 324 in FIG. 23 via a second air connection point 320. The foot pedal 324 may contain a valve which, when depressed, allows the operator a means of hands-free activation of the machine. When the foot pedal 324 is depressed, a valve inside allows air to flow from the main supply, through the foot pedal and is directed back into the machine via a third air input 322 on the machine. That air reentering the machine is directed through the pneumatic plumbing inside the machine to actuate one cycle of the machine.

The foot pedal 324 may have two air connection points which allows air into the foot pedal 324 which allows air to flow out for cycling the machine 300. Depressing the foot pedal 324 may open a valve allowing air to flow through and into the machine 300. The machine 300 itself may include an additional air input to supply the entire described operation with compressed air.

The device 300 may include a plug storage body 326 that is connectable to the housing 302 and having a cavity or hopper therein for storing a plurality of plugs 25. The device 300 may be configured to extract plugs 25 from the cavity, one at a time, for insertion into the vent opening 23 on the slider 18.

Referring now to FIGS. 25-28, several internal components (e.g., components typically located within the housing 302) are depicted, including a slider cradle 328, a plug feed wheel 330, a push rod 332, and a pair of needle wipers 334. The slider cradle 328 includes a base surface 336 formed on a main body 338, and a pair of projecting bodies 340 extending from the main body 338 in opposed relation to each other. The space between the projecting bodies 340 is sized to accommodate the slider 18, such that when the slider 18 is placed between the projecting bodies 340, the vent opening 23 faces toward the plug feed wheel 330. The slider 18 may include a vent plug body 27 extending axially from a rear surface of the slider 18 and between a pair of slider sidewalls 29. When the slider 18 is inserted within the slider cradle 328, the vent plug body 27 may be received between a pair of stabilizing walls 342, which extend upwardly from the main body 338 between the vent plug body 27 and a respective slider sidewall 29. The device 300 may further include a pair of lateral support walls 344 that create a space to accommodate the slider 18.

The plug feed wheel 330 is in operative communication with the plug storage body 326 to receive vent plugs 25 therefrom. The plug feed wheel 330 is mounted on an axle 346 that rotates about a rotation axis 348, and includes a first surface and an opposing second surface, each of which may be generally perpendicular to the rotation axis 348. A plurality of openings 350 may extend between the first surface and the second surface and may be spaced apart from each other, as well as being spaced from the rotation axis 348 by a substantially equal radial distance. In this regard, the openings 350 may be arranged on the plug feed wheel 330 such that an imaginary circle could pass through each of the openings 350. The plug feed wheel 330 may include six (6) indexed semi-circular slots around the outer circumference of the feed wheel. The radius of these slots may be the same as (or slightly larger than) the outer diameter of the porous vent plugs. The plug feed wheel 330 and slots protrude slightly into the hopper containing the vent plugs. As the plug feed wheel 330 rotates across the bottom of the vent plug hopper, a vent plug may be picked up/loaded onto the feed wheel 330.

The indexed feed plug wheel 330 may be mounted on an axel 346 which has a unique and specifically contoured piece of plastic mounted on the rear. The axel, and therefore indexed feed plug wheel 330 and contoured plastic piece have a spring mounted to them which may place rotational pressure on the axel and attached parts. The axel and contoured plastic piece may be prevented from rotating by a piston 358, which the contoured plastic piece sits/presses against. When the operator depresses the foot pedal 324, as the operation cycle begins, the piston 358 is driven forward pneumatically and completely clears the contoured plastic piece. This allows the contoured plastic piece, as well as the axel 346 it is mounted on to rotate clockwise. As the operation cycle ends, the piston 358 moves rearward to its starting position. The unique contouring shape of the plastic piece allows the returning piston to rotate the plastic piece and axel counterclockwise to the original starting position. It is at this point, during the counterclockwise rotation of the plastic piece and axel, that a body attached to the plug feed wheel 330 or in operative communication with the plug feed wheel 330 allows the plug feed wheel 330 to rotate counterclockwise with the axel.

Figure 26:
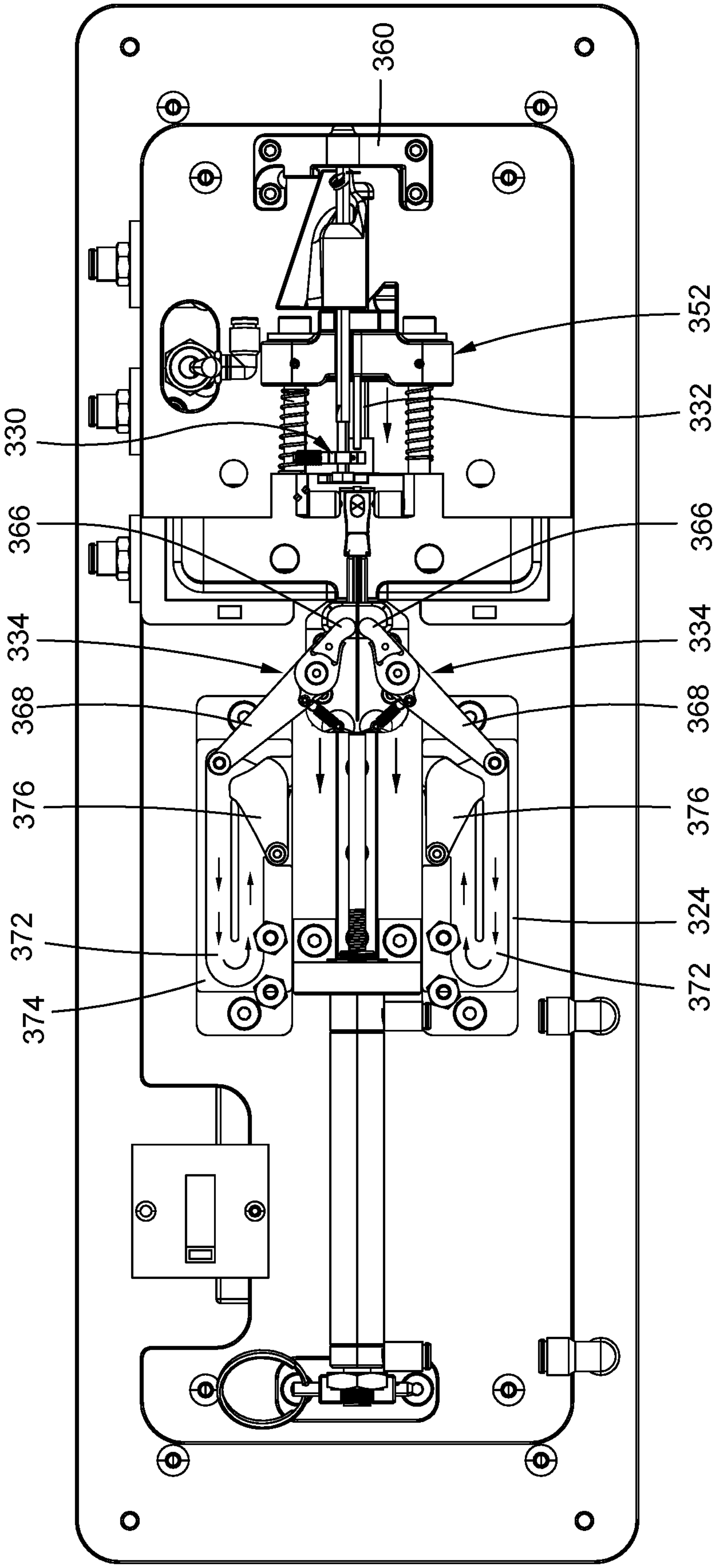
FIG. 26 is a top view of internal components of the device depicted in FIG. 23 for inserting the vent plug and wiping the needle with lubricant.
Figure 27:
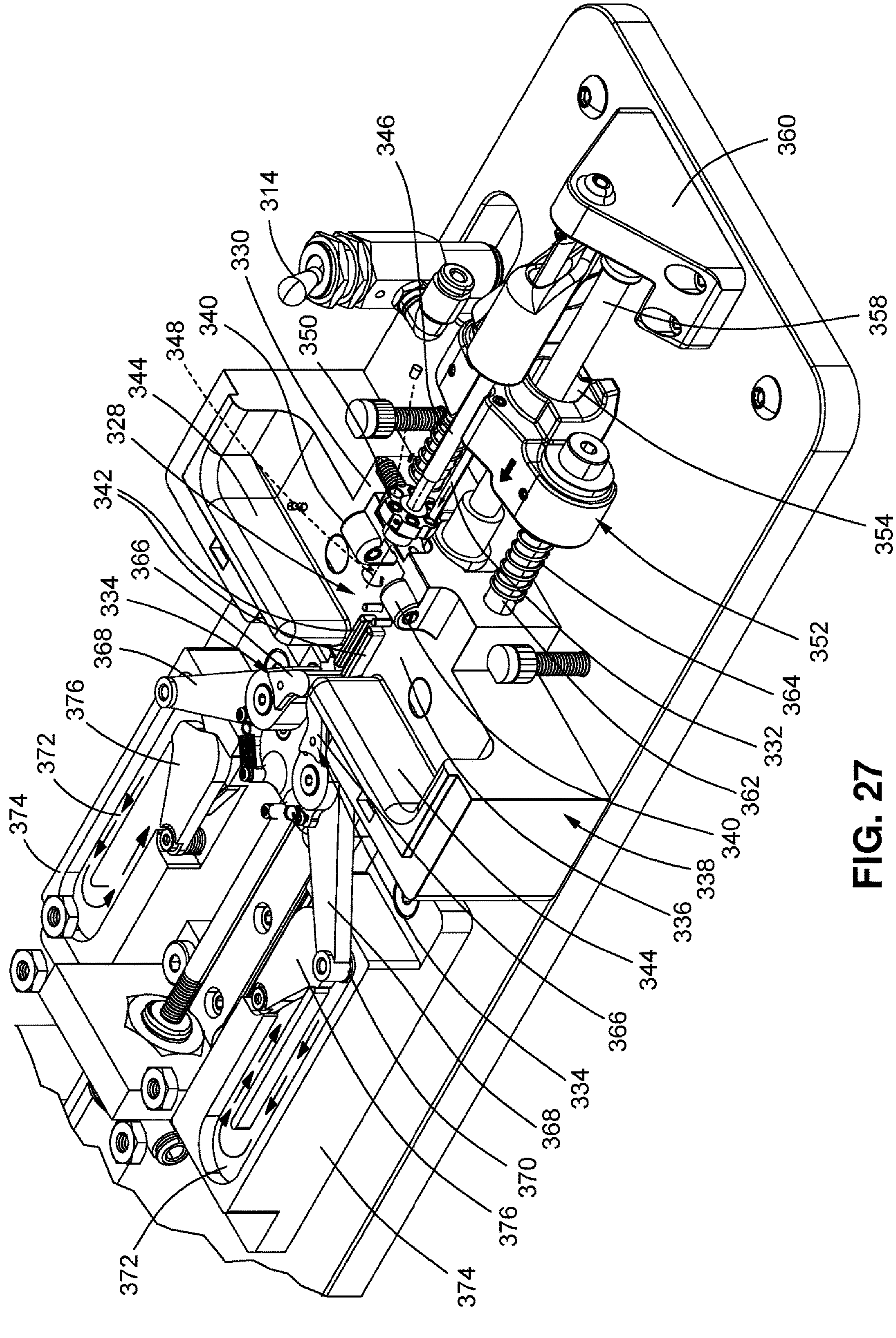
FIG. 27 is an upper perspective view of the components depicted in FIG. 26.
Figure 28:
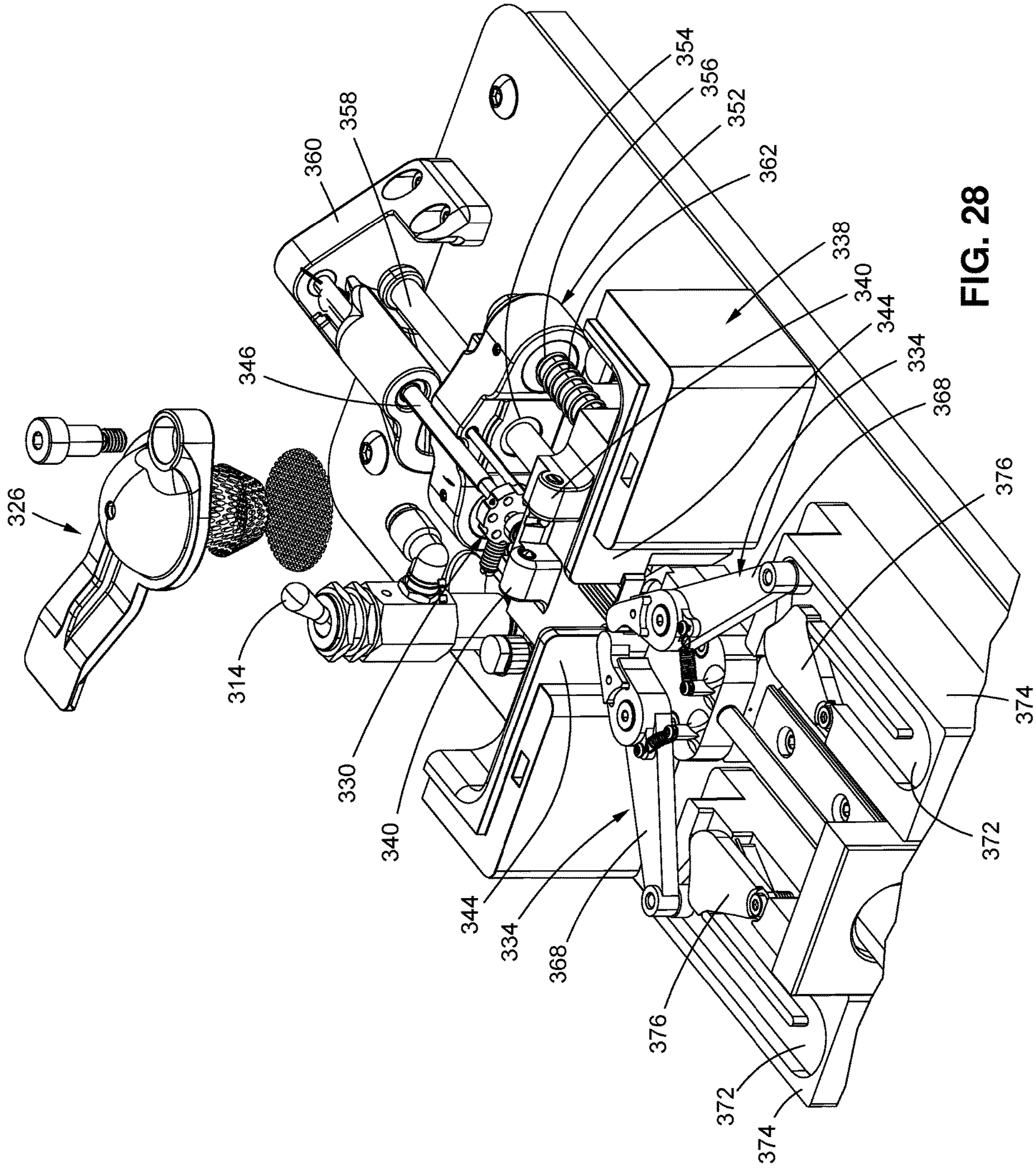
FIG. 28 is a partial view of the internal components included in the device depicted in FIG. 23.
Figure 29:
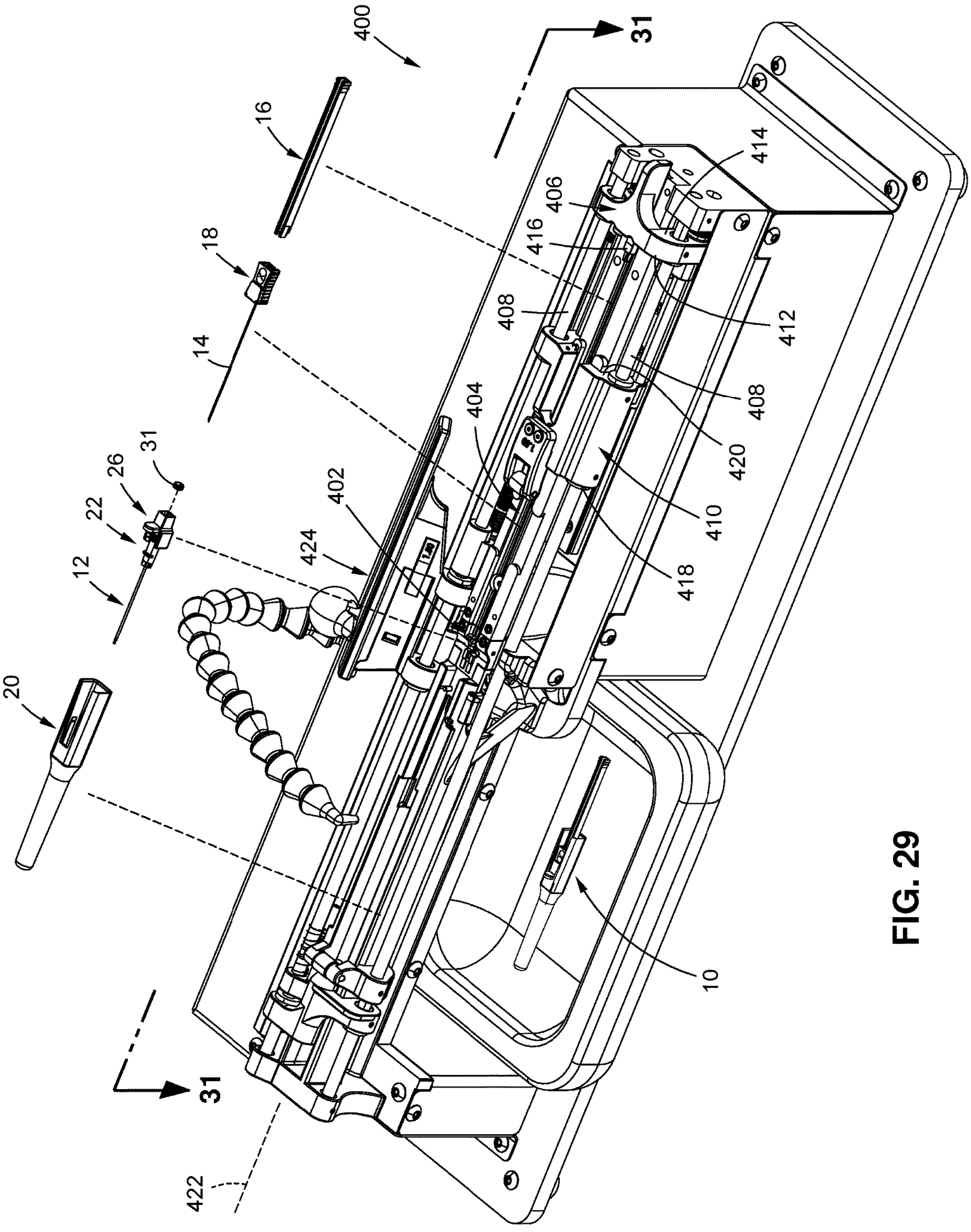
FIG. 29 is a front, upper perspective view of a final assembly device for connecting a sheath to a slider, and inserting the needle through a connector, a hub and a catheter, and placing a cover over the needle and catheter.
Figure 30:
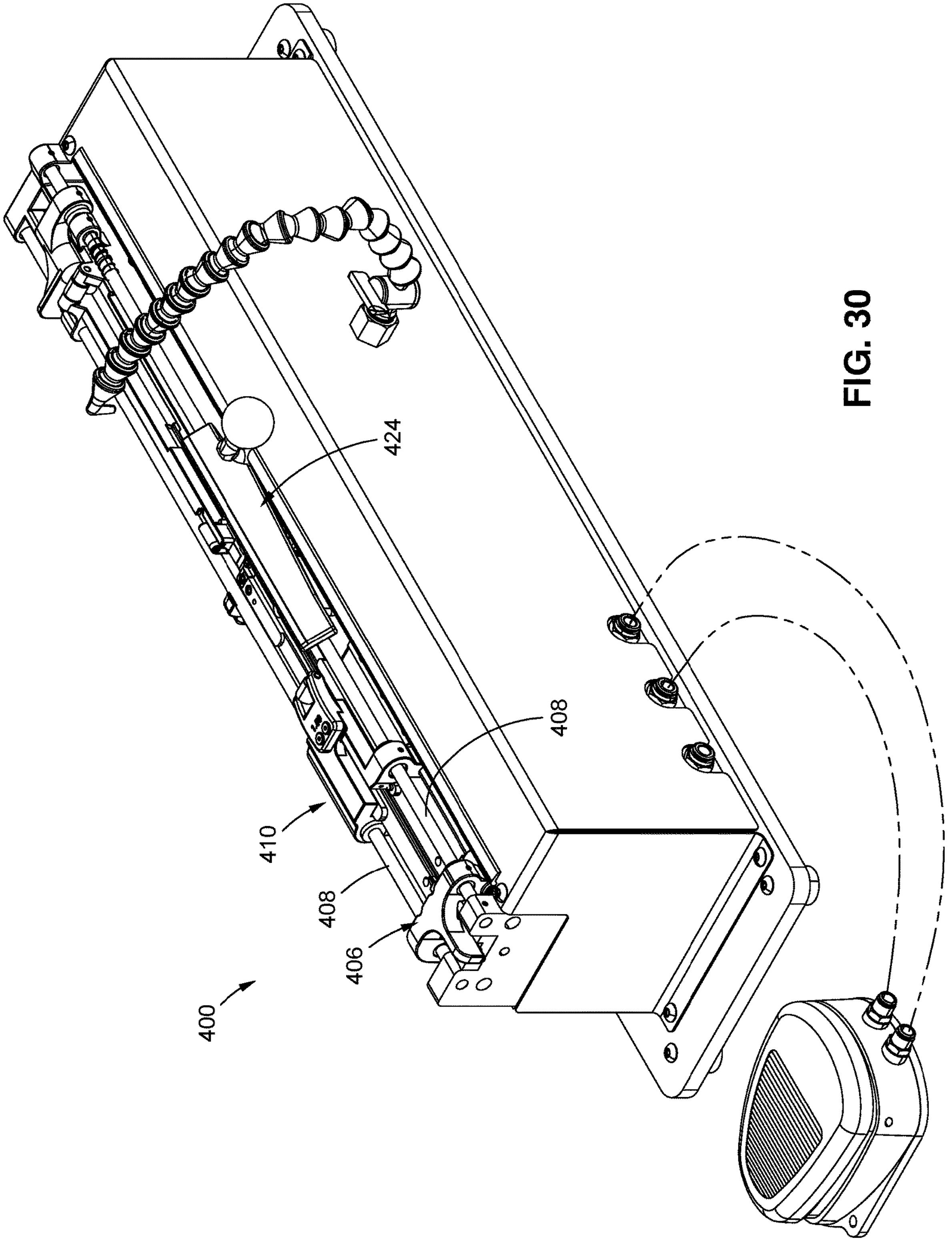
FIG. 30 is a rear, upper perspective view of the final assembly device depicted in FIG. 29.
Figure 31:
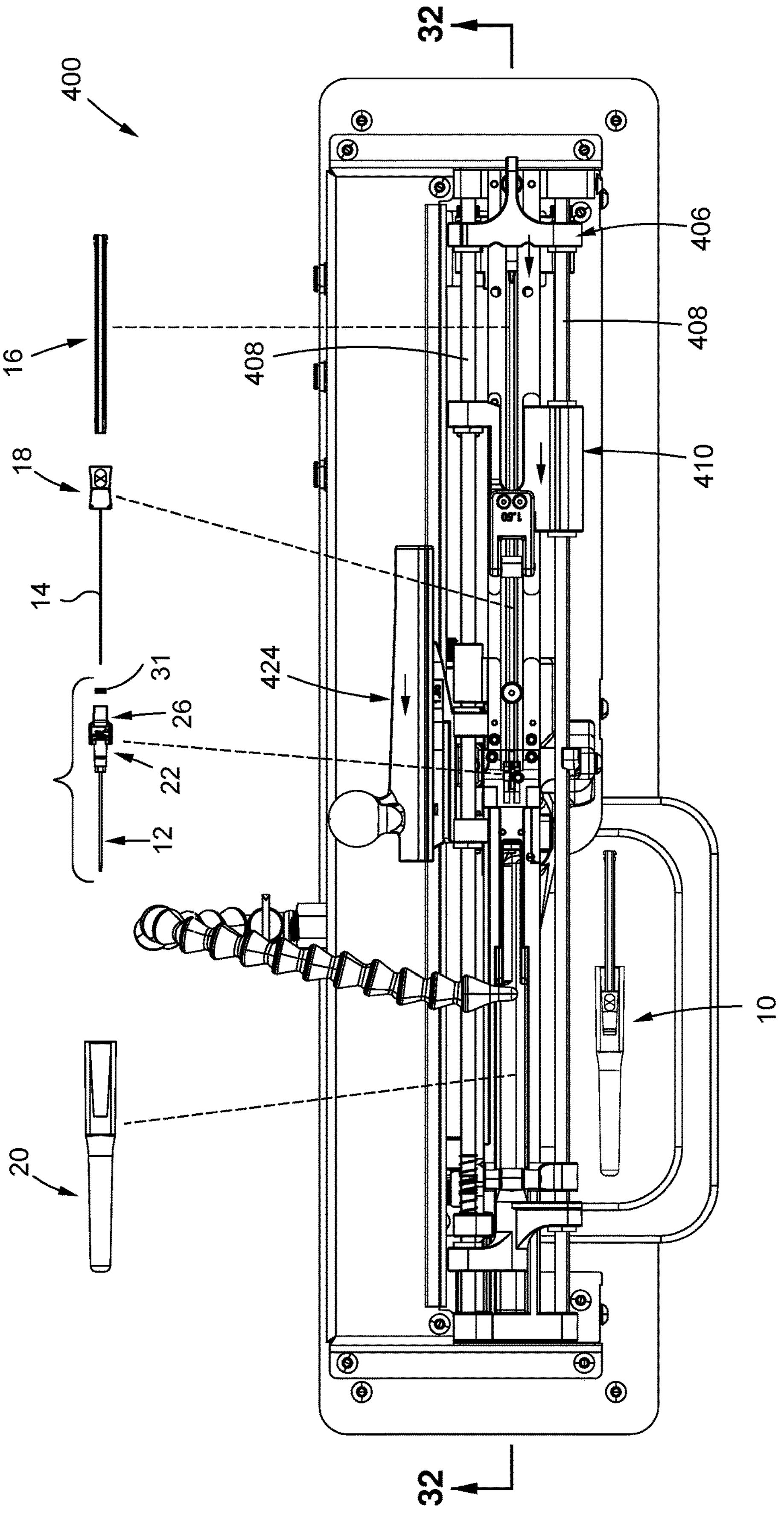
FIG. 31 is a top view of the final assembly device depicted in FIG. 29.
Figure 32:
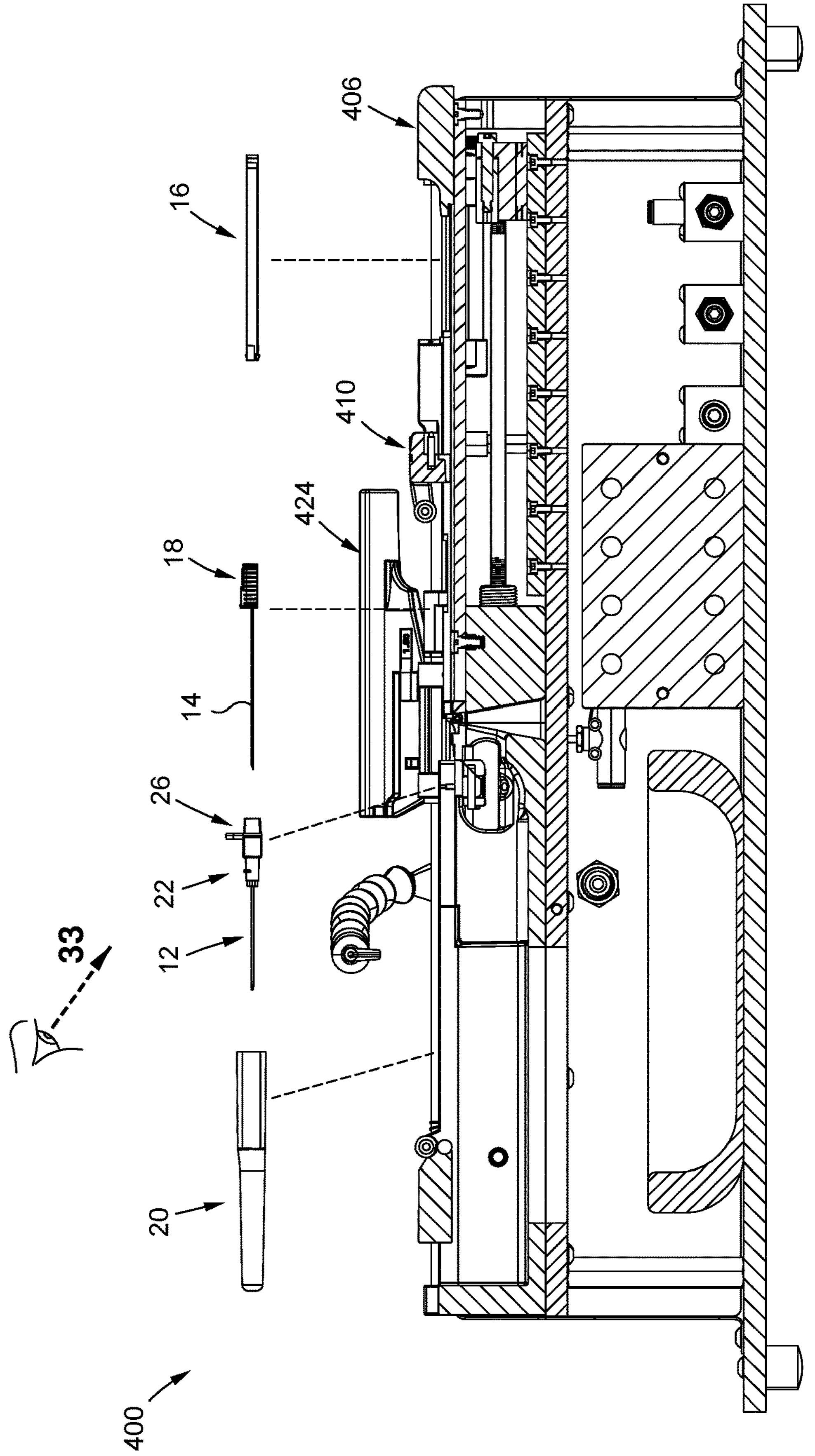
FIG. 32 is a front, cross sectional view of the final assembly device depicted in FIG. 29.
Figure 33:
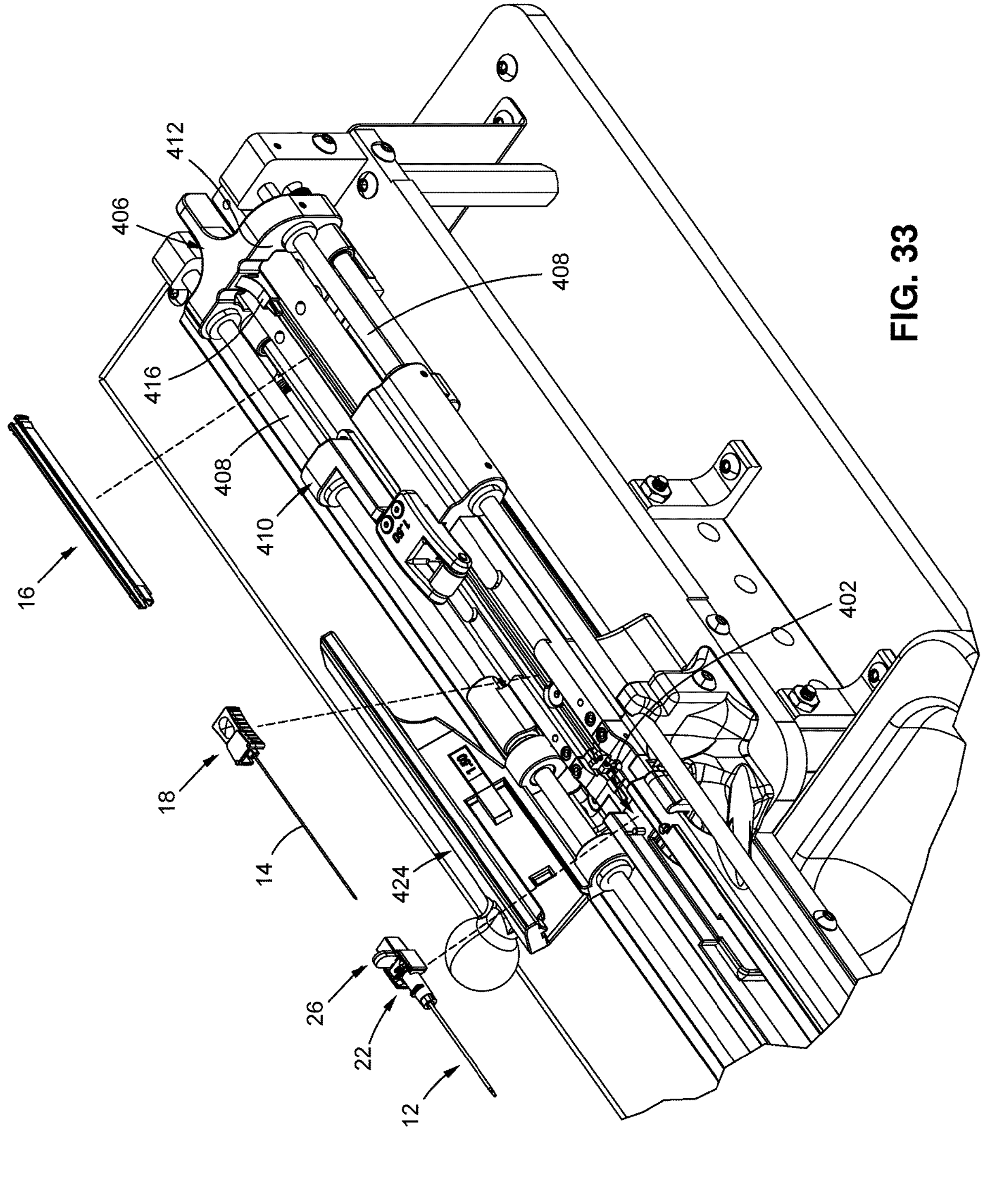
FIG. 33 is a partial, upper perspective view of the final assembly device depicted in FIG. 29 illustrating placement of the sheath, slider, needle, connector, hub, and catheter in the device prior to assembly.
Figure 34:
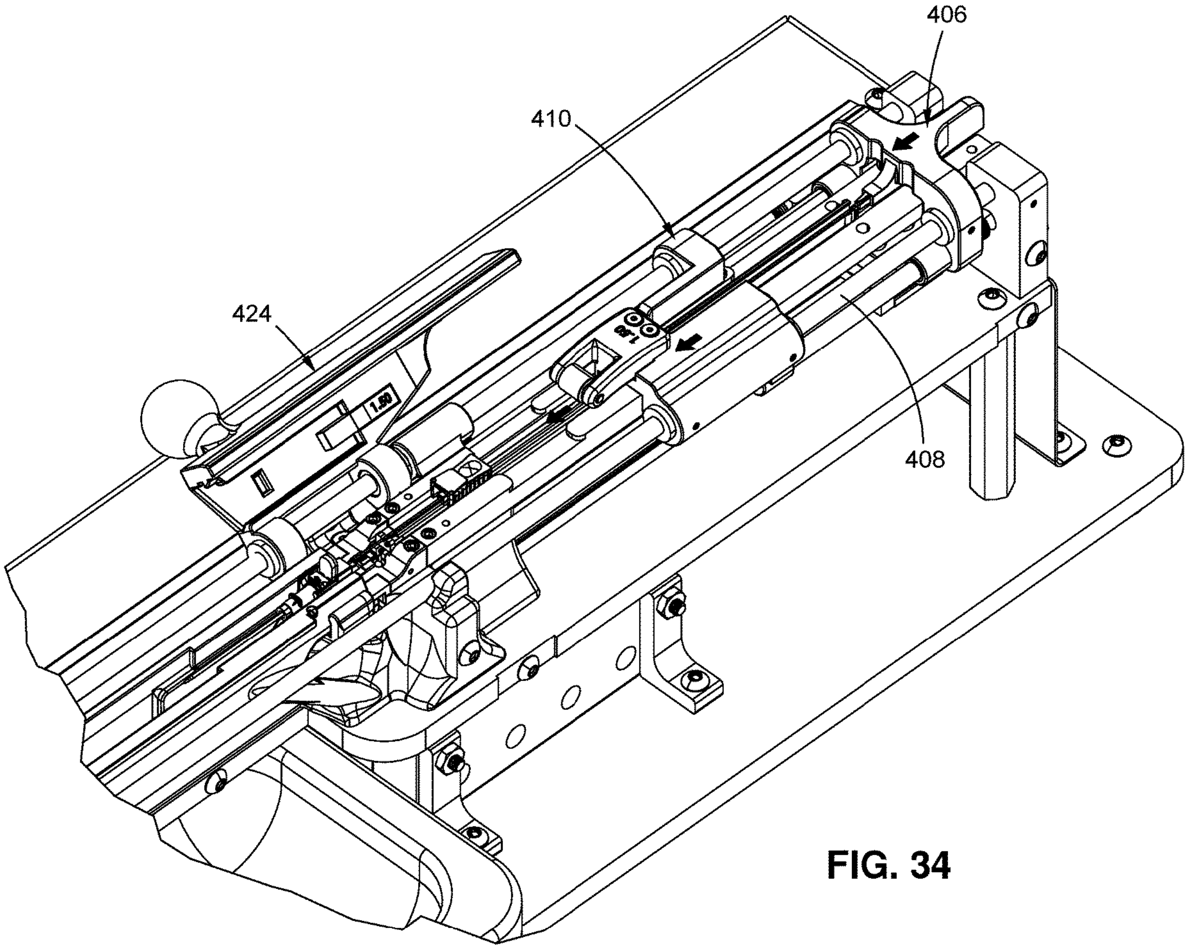
FIG. 34 is a partial, upper perspective view of the final assembly device depicted in FIG. 29, illustrating movement of a sheath holder and an intermediate carriage used in the assembly process.
Figure 35:
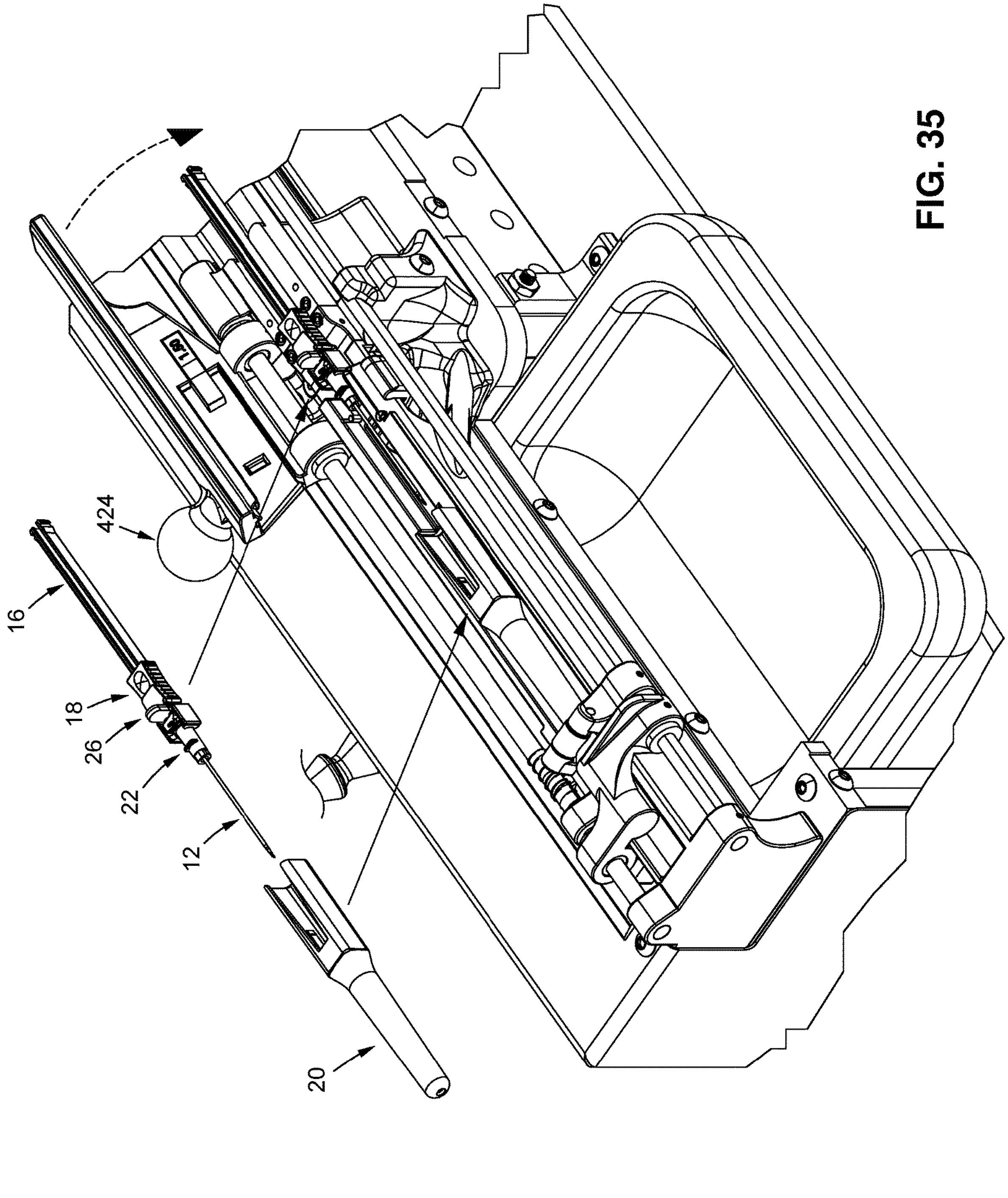
FIG. 35 is a partial, upper perspective view of the final assembly device depicted in FIG. 29, illustrating pivotal movement of a slider used to insert an assembled passive protector into a cover.
Figure 36:
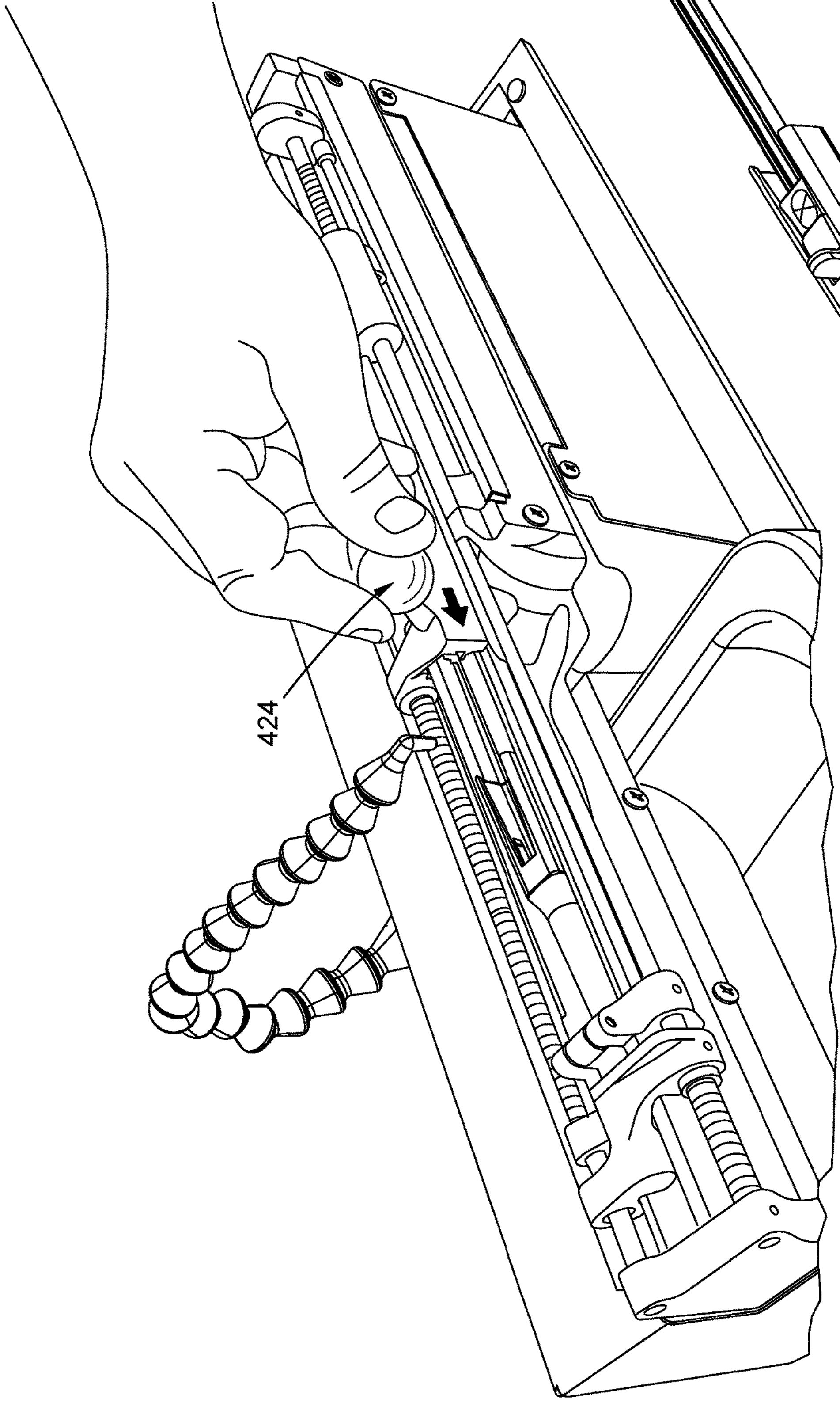
FIG. 36 is a partial, upper perspective view of the final assembly device depicted in FIG. 29, illustrating axial movement of a slider used to insert the assembled passive protector into the cover.
Figure 37:
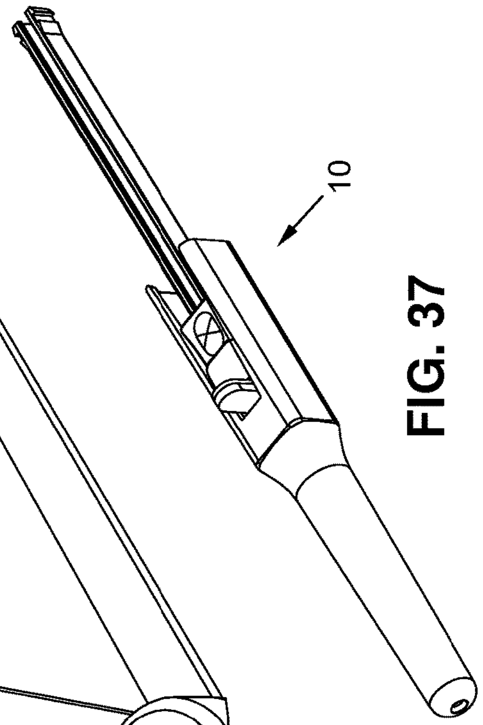
FIG. 37 is an upper perspective view of the assembly universal passive protector assembled using the final assembly device depicted in FIG. 29.

The push rod 332 or plunger is connected to a drive carriage 352 and is configured for pushing a vent plug 25 from the plug feed wheel 330 into the vent opening 23 when the vent plug 25, vent plug opening 23, and push rod 332 are coaxially aligned with each other along a vent insertion axis defined by the push rod 332. The push rod 332 may include an elongate body that extends axially along the vent insertion axis, and includes a fixed end portion mounted to the drive carriage 352 and a free end portion opposite the fixed end portion. The drive carriage 352 includes a central opening 354, and a pair of lateral openings 356 on respective sides of the central opening 354. The central opening 354 accommodates a central shaft 358 that extends between the main body 338 and a rear mount 360. Each lateral opening 356 accommodates a respective lateral shaft 362 that extends between the main body 338 and the drive carriage 352. The drive carriage 352 may reciprocate along the central shaft 358 between a retracted position, as shown in FIGS. 26 and 27, and a pushing position, with the drive carriage 352 moving toward the main body 338 as the drive carriage 352 moves from the retracted position toward the pushing position, and the drive carriage 352 moving away from the main body 338 as the drive carriage 352 moves from the pushing position toward the retracted position. Each lateral shaft 362 may be fixed to the drive carriage 352 and movable relative to the main body 338, such that a portion of each lateral shaft 362 moves into the main body 338 as the drive carriage 352 moves from the retracted position toward the pushing position, and a portion of each lateral shaft 362 moves away from the main body 338 as the drive carriage 352 moves from the pushing position toward the retracted position. A coil spring 364 may extend around each lateral shaft 362 and may be energized as the drive carriage 352 moves from the retracted position toward the pushing position to impart a biasing force on the drive carriage 352 to urge the drive carriage 352 toward the release position.

The push rod 332 may be pneumatically actuated, which pushes a vent plug out of the indexed cylinder slot and into the rear of the flash trap 18. A covered vent plug hopper 326 may be loaded through the use of a small, fixed volume scoop. The loaded vent plugs may sit below the rim of the hopper to allow the hopper lid to fully close and to ensure proper vent plug loading into the indexed rotating cylinder. Once the hopper door is fully shut, a toggle switch 314 in may be switched to the "on" position, which may allows for some of the supplied air to be directed into the vent plug hopper chamber. This air, blowing into the hopper 326, may agitate the vent plugs to avoid settling and allow all plugs to have a chance to be picked up by the indexed vent plug insertion wheel/cylinder 330, which may be located and rotates directly under the hopper 326 and is partially exposed to the hopper 326 through a small opening. The hopper lid may include a mesh screen on the bottom of it to keep the vent plugs toward the bottom of the hopper so they may be more easily picked up by the indexed wheel/cylinder and allows for airflow around the vent plugs and hopper chamber. The air directed into the hopper chamber may be allowed to escape through a small vent hole on the top of the hopper lid. Every time the foot pedal 324 is depressed the indexed vent plug cylinder 330 may rotate one position, having picked up a vent plug in the upper exposed of six (6) slots. As the machine is cycled and the now loaded vent plug cylinder rotates, the indexed slot toward the bottom position (approx. 7' oclock position) will be aligned with a through-hole and the rear of the flash trap 18 where the vent plug is inserted. Finally, a pin 32 may be pneumatically actuated, which pushes the vent plug out of the indexed cylinder slot and into the rear of the flash trap 18.

The needle wipers 334 include a pair of wiper bodies 366, each being attached to a corresponding wiper arm 368 that is connected to a pin 370 which travels with a groove 372 formed within a guide body 374. A camming body 376 may be pivotally connected to the guide body 374 and may pivot between a blocking position and a passing position. The camming body 376 may also be connected to a spring to urge the camming body 376 toward the blocking position. Upon actuation, the pins 370 travel in the direction shown by arrows depicted in the grooves 372. The camming body 376 is configured to allow the pins 370 to pass in the direction of the arrows, and may prevent movement of the pins 370 in the direction opposite to that of the arrows. In particular, the camming body 376 may be pivotally connected to the guide body 374, such that contact between the pin 370 and a respective camming body 376 as the pin 370 travels in the preferred direction of the groove 372 causes the camming body 376 to pivot away from the groove 372 (e.g., toward the passing position) to allow for passage of the pin 370 through the groove 372. After the pin 370 passes through the groove 372, the camming body 376 may return to its original position.

Referring now to FIGS. 29-37, there is depicted a final assembly device 400 capable of facilitating assembly of the sheath 16 to the slider 18, and the slider 18 to the connector 26, and the connector 26 to the cover 20. The connection of the sheath 16, the slider 18 and the connector 26 may be achieved in one motion, while the connection of the cover 20 to the connector 26 may be achieved in a subsequent motion.

The device 400 is loaded by placing a spring in the connector 26 and placing the hub 22 between the arms of the connector 26 to define a connector sub-assembly, which is placed in a connector holder 402. The slider 18, having already been connected to the needle 14, is placed in a slider holder 404, and the sheath 16 is placed in a sheath holder 406. The device 400 includes a pair of opposed rails 408 that extend longitudinally along the device 400, with the sheath holder 406 being moveable along the rails 408 between a loading position and an actuated position. The device 400 additionally includes an intermediate carriage 410 that is also moveably connected to the rails 408. A pair of coil springs may be connected to respective rails 408 and located between the sheath holder 406 and the intermediate carriage 410.

The sheath holder 406 may include a forward surface 412 and a rearward surface 414, with a pair of openings extending between the forward and rearward surfaces 412, 414 to accommodate the pair of rails 408. A finger 416 may be formed on the sheath holder 406, with the finger 416 extending from the forward surface 412 and configured to engage with the sheath 16 as the sheath 16 is loaded on the sheath holder 406. In this regard, the finger 416 may extend into the sheath cavity of the sheath 16 when the sheath 16 is loaded onto the sheath holder 406.

The sheath holder 406 may be driven pneumatically and may be connected to a pneumatic, double-acting air cylinder/piston by way of a threaded shaft. When an operator depresses the foot pedal to begin an operation cycle, the air cylinder moves from right to left/forward, pulling the threaded shaft and the attached sheath driver forward.

The intermediate carriage 410 includes a forward surface 418 and a rearward surface 420, with a pair of openings extending between the forward and rearward surfaces 418, 420 to accommodate the pair of rails 408. The intermediate carriage 410 may include a recess or void to accommodate the sheath 16 during use of the device 400, as will be described in more detail below.

Once a sheath 16 is loaded on the sheath holder 406, the device 400 may be actuated to cause the sheath holder 400 to move from the loading position toward the actuated position, wherein the sheath holder 406 moves along the rails 408 (e.g., along an assembly axis 422 parallel to the rails 408) toward the intermediate carriage 410. As the distance between the sheath holder 406 and the intermediate carriage 410 decreases, the springs between the sheath holder 406 and intermediate carriage 410 may compress until the intermediate carriage 410 begins to move concurrently with the sheath holder 406.

As the sheath holder 406 continues toward the actuated position, the intermediate carriage 410 engages with the slider 18 and moves the slider 18 toward the connector 26. Continued movement of the sheath holder 406 toward the actuated position causes the slider 18 to engage and connect with the connector 26, and the sheath 16 to engage and connect with the slider 18. Each of the connector 26, the slider 18, and the sheath 16 are configured for press-fit engagement, such that the force applied by the sheath holder 406, and through the intermediate carriage 410 applies sufficient force to effectuate such press-fit engagement. Once the sheath 16, slider 18, and connector 26 are engaged (at the actuated position), the sheath holder 406 reverses its movement from the actuated position toward the loading position to release the newly formed sub-assembly.

A manually actuated slide-press 424 is then used to slide the sub-assembly into the cover 20. In particular, the manually slide-press 424 is first pivoted around one of the rails 408 from an open position toward a closed position, wherein the slide-press 424 engages with the sub-assembly. The slide-press 424 may then be moved along the rail 408 to move the sub-assembly into the cover 20 to achieve a finished, complete assembly. Continued movement of the completed assembly along the rails 408 causes the finished assembly to drop into a collection tray for easy retrieval.

A pneumatically driven piston may advance the stem through and with the needle-flash trap subassembly into and through the jaws, spring, hub, ferrule and catheter. The device is now assembled and sits in a channel in the final assembly fixture just behind the cover. The cover is loaded by hand; the front of the cover has a hole in the front which is aligned into a spring-loaded retainer and the rear of the cover sits on two small "shelves" on either side of the fixture. The spring-loaded retainer presses the cover rearwards holding it in place on the shelves. The final step in the process is for the operator to grab a ball handle and close a cover over the entire assembled device. Features inside the cover interact with features on the device as the operator moves the handle from right to left. This advances the device into the cover and pushes the device and cover off the shelves, which were holding the cover, and therefore entire device up. Once off and past the shelves, the final assembly fixture widens out enough to allow the entire device to gravity fall into a collection trey.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show more details than is necessary for a fundamental understanding of the disclosure, the description taken with the drawings making apparent to those skilled in the art how the several forms of the presently disclosed disclosure may be embodied in practice.

What is claimed is:

1. A method of assembling a low-profile passive protector, the method comprising the steps of:

forming a hard tubular portion and a soft tubular portion to form an integral catheter having a prescribed contour;

pressing a ferrule into the catheter;

attaching a hub to the catheter such that the ferrule facilitates attachment of the hub to the catheter;

inserting a vent plug into a slider; and connecting the slider to the catheter.

2. The method of assembling a low-profile passive protector of claim 1, wherein the forming step includes placing the hardened tubular portion inside the soft tubular portion.

3. The method of assembling a low-profile passive protector of claim 2, further comprising the step of inserting a mandrel through the hard tubular portion and the soft tubular portion.

4. The method of assembling a low-profile passive protector of claim 3, further comprising the step of moving the mandrel toward a forming body to facilitate contact between the forming body and the hard tubular portion.

5. The method of assembling a low-profile passive protector of claim 4, further comprising the step of heating the forming body to facilitate melting of at least a portion of the hard tubular portion when the hard tubular portion is in contact with the forming body.

6. The method of assembling a low-profile passive protector of claim 1, wherein the pressing step includes placing the ferrule on a mandrel having a pin insertable through the ferrule and the catheter.

7. The method of assembling a low-profile passive protector of claim 1 wherein the ferrule used in the pressing step includes a wide portion and a narrow portion, the narrow portion being pressable into the soft tubular portion of the catheter.

8. The method of assembling a low-profile passive protector of claim 7, further comprising the step of moving the mandrel toward a gripping element configured to press a segment of the soft tubular portion over the narrow portion of the ferrule in response to such movement of the mandrel relative to the gripping element.

9. The method of assembling a low-profile passive protector of claim 8, further comprising the step of aligning the mandrel with the gripping element using magnetic attraction between the mandrel and a lower press plate associated with the gripping element.

10. The method of assembling a low-profile passive protector of claim 9, further comprising the step of raising the lower press plate toward the gripping element.

11. The method of assembling a low-profile passive protector of claim 1, wherein the hub used in the attaching step includes a proximal end face, a distal end face, internal opening extending between the proximal end face and the distal end face and extending around a central axis, and an internal rib extending into the opening from an inner surface thereof.

12. The method of assembling a low-profile passive protector of claim 11, wherein the attaching step includes loading the ferrule and catheter onto a core pin, and placing the hub over the core pin and catheter such that a majority of the core pin and the catheter protrude from the hub, and the ferrule is located in the internal opening of the hub.

13. The method of assembling a low-profile passive protector of claim 12, wherein the attaching step further includes pressing the ferrule beyond the internal rib.

14. The method of assembling a low-profile passive protector of claim 1, wherein the inserting step includes aligning the vent plug with a push rod.

15. The method of assembling a low-profile passive protector of claim 14, wherein the alignment of the vent plug with the push rod includes rotating a plug feed wheel configured to carry the vent plug, until the vent plug is aligned with the push rod, the push rod being configured to be moveable relative to the plug feed wheel, the vent plug, and the slider.

16. The method of assembling a low-profile passive protector of claim 15, further comprising the step of actuating the push rod to push the vent plug into the vent plug opening.

17. The method of assembling a low-profile passive protector of claim 1, wherein the slider includes a hypodermic needle attached thereto, the method further comprising the step of wiping the hypodermic needle with a lubricant.

18. The method of assembling a low-profile passive protector of claim 1, further comprising the steps of:

placing the slider in a slider holder;

placing a sheath in a sheath holder; and causing the sheath holder to move toward to the slider holder to facilitate engagement between the sheath and the slider.

19. The method of assembling a low-profile passive protector of claim 1, further comprising the steps of:

placing a connector having a pair of arms in a connector holder;

placing the slider in a slider holder aligned with a carriage moveable relative to the connector holder; and causing the carriage to move to carry the slider into engagement with the connector.

20. The method of assembling a low-profile passive protector recited in claim 1, further comprising the steps of:

forming a sub-assembly including the slider, a sheath, and a connector, with the slider being disposed between the sheath and the connector; and connecting a cover to the sub-assembly using a manually actuated slide-press configured to slide the sub-assembly into the cover.

* * * * *